US006640636B1

United States Patent
Toda

(10) Patent No.: US 6,640,636 B1
(45) Date of Patent: Nov. 4, 2003

(54) ULTRASOUND RADIATING AND RECEIVING DEVICE

(76) Inventor: Kohji Toda, 1-49-18 Futaba, Yokosuka 239-0814 (JP)

( * ) Notice: Subject to any disclaimer, the term of this patent is extended or adjusted under 35 U.S.C. 154(b) by 0 days.

(21) Appl. No.: 10/153,564

(22) Filed: May 20, 2002

(51) Int. Cl.[7] ............................................... G01D 21/00
(52) U.S. Cl. ..................... 73/651; 367/155; 310/313 A; 310/313 B; 333/154; 333/193
(58) Field of Search ............................. 73/651, 514.34; 367/155, 157; 310/313 A, 313 B, 313 R, 313 D; 333/150, 151, 154, 193, 194

(56) References Cited

U.S. PATENT DOCUMENTS

| 3,676,721 A | * | 7/1972 | Van Den Heuval et al. .. 310/313 B |
| 4,456,847 A | * | 6/1984 | Minagawa et al. ...... 310/313 R |
| 4,491,811 A | * | 1/1985 | Niitsuma et al. ............ 333/151 |
| 4,531,107 A | * | 7/1985 | Okamoto et al. ............ 333/194 |
| 4,571,519 A | * | 2/1986 | Kawabata et al. ...... 310/313 A |
| 4,572,709 A | * | 2/1986 | Weirich et al. .......... 310/313 A |

* cited by examiner

Primary Examiner—Richard A. Moller

(57) ABSTRACT

An ultrasound radiating and receiving device comprises a piezoelectric substrate, an interdigital arrangement of first and second comb-shaped electrodes, and a counter electrode. The interdigital arrangement is mounted on an upper end surface of the piezoelectric substrate. The counter electrode is formed on a lower end surface of the piezoelectric substrate, and is in contact with a surface-part of a material through the lower end surface of the counter electrode. When an input electric signal is applied between the first comb-shaped electrode and the counter electrode, a longitudinal wave is radiated into the material through the surface-part of the material along the direction vertical to the lower end surface of the piezoelectric substrate. If the longitudinal wave is reflected at an object located inside the material, a reflected longitudinal wave is detected between the second comb-shaped electrode and the counter electrode as a delayed electric signal.

29 Claims, 24 Drawing Sheets finger overlap-zone finger overlap-zone

ULTRASOUND RADIATING AND RECEIVING DEVICE

BACKGROUND OF THE INVENTION

1. Field of the Invention

The present invention relates to a device for radiating an ultrasound into a material and receiving a reflected ultrasound by means of using a piezoelectric substrate, an interdigital arrangement of two comb-shaped electrodes formed on an upper end surface of the piezoelectric substrate, a counter electrode formed on a lower end surface of the piezoelectric substrate.

2. Description of the Prior Art

A thickness mode piezoelectric transducer with parallel plate-like electrodes is commonly used for radiating an ultrasound into a liquid. When receiving a reflected ultrasound from the liquid, such a conventional type of transducer needs, for example, a circulator in order to separate a delayed electric signal from an input electric signal, because the conventional type of transducer is used both as input- and output electrodes. Accordingly, such the conventional type of transducer has a difficulty in quick response measurement, and a complicated circuit-construction. In addition, such the conventional type of transducer has a difficulty in scanning operation.

On the other hand, an interdigital transducer on the piezoelectric substrate operates at a liquid-solid boundary as a leaky wave transducer for bulk wave radiation into the liquid. The leaky SAW traveling on a sufficiently thick substrate compared with the wavelength has only one mode without velocity dispersion. Such the interdigital transducer for the leaky SAW has a difficulty in making the radiation angle vertical.

SUMMARY OF THE INVENTION

An object of the present invention is to provide an ultrasound radiating and receiving device capable of making an interdigital transducer act as a thickness mode transducer.

Another object of the present invention is to provide an ultrasound radiating and receiving device operating with a quick response.

Another object of the present invention is to provide an ultrasound radiating and receiving device need not a circulator, and so on.

Another object of the present invention is to provide an ultrasound radiating and receiving device capable of scanning operation.

Another object of the present invention is to provide an ultrasound radiating and receiving device capable of imaging of an object in a material.

Another object of the present invention is to provide an ultrasound radiating and receiving device capable of making the radiation angle vertical.

Another object of the present invention is to provide an ultrasound radiating and receiving device capable of low electric power consumption.

Another object of the present invention is to provide an ultrasound radiating and receiving device capable of radiating an ultrasound into a cellular tissue and receiving a reflected signal.

Another object of the present invention is to provide an ultrasound radiating and receiving device excellent in durability and manufacturing.

A still other object of the present invention is to provide an ultrasound radiating and receiving device easy in use and having a small size which is very light in weight and has a simple structure.

According to one aspect of the present invention there is provided an ultrasound radiating and receiving device comprising a piezoelectric substrate, first and second comb-shaped electrodes formed on an upper end surface of the piezoelectric substrate, and a counter electrode formed on a lower end surface of the piezoelectric substrate. The counter electrode is in contact with a surface-part of a material through the lower end surface of the counter electrode. The first- and second comb-shaped electrodes form an interdigital arrangement.

If an input electric signal is applied between the first comb-shaped electrode and the counter electrode, a longitudinal wave is radiated into the material through the surface-part of the material along the direction vertical to the lower end surface of the piezoelectric substrate. The, longitudinal wave is reflected at an object located inside the material. And then, a reflected longitudinal wave is detected between the second comb-shaped electrode and the counter electrode as a delayed electric signal.

According to another aspect of the present invention there is provided an amplifier between the first- and second comb-shaped electrodes. Thus, the delayed electric signal is amplified via the amplifier, and supplied to the first comb-shaped electrode as the input electric signal again.

According to another aspect of the present invention there is provided an ultrasound radiating and receiving device, wherein the opposite surface-part of the material acts as the object.

According to another aspect of the present invention there is provided an ultrasound radiating and receiving device, wherein the ratio of the interdigital periodicity of the interdigital arrangement to the thickness of the piezoelectric substrate is smaller than four times the ratio of the longitudinal wave velocity in the material to the longitudinal wave velocity in the piezoelectric substrate.

According to another aspect of the present invention there is provided an ultrasound radiating and receiving device, wherein increasing the number of electrode-finger pairs in the interdigital arrangement makes the directionality of the longitudinal wave sharper under a condition that the total amount of all the finger-areas of the first comb-shaped electrode is constant.

According to another aspect of the present invention there is provided an ultrasound radiating and receiving device, wherein the material is a liquid matter.

According to another aspect of the present invention there is provided an ultrasound radiating and receiving device, wherein the material is a cellular tissue.

According to another aspect of the present invention there is provided a polymer film, with which the lower end surface of the counter electrode is coated.

According to another aspect of the present invention there is provided a scanning unit composed of groups $X_i$ (i=1, 2, . . . , n) of switches, which correspond to the electrode-fingers of the first comb-shaped electrode, respectively. One and the next of the groups $X_i$ have common switches each other except the first switch of the one of the groups $X_i$ and the last switch of the next of the groups $X_i$.

If input electric signals are applied between the first comb-shaped electrode and the counter electrode via the groups $X_i$ in turn, longitudinal waves are radiated along the direction vertical to the lower end surface of the piezoelectric substrate into the material in the form of a scanned ultrasound beam as a whole. The scanned ultrasound beam is reflected at the object, and detected between the second comb-shaped electrode and the counter electrode detecting as a scanned electric signal.

According to another aspect of the present invention there are provided a first scanning unit composed of groups $X_i$ (i=1, 2, ..., n) of switches corresponding to the electrode-fingers of the first comb-shaped electrode, respectively, and a second scanning unit composed of groups $Y_i$ (i=1, 2, ..., n) of switches corresponding to the electrode-fingers of the second comb-shaped electrode, respectively. One and the next of the groups $X_i$ have common switches each other except the first switch of the one of the groups $X_i$ and the last switch of the next of the groups $X_i$. In the same way, one and the next of the groups $Y_i$ have common switches each other except the first switch of the one of the groups $Y_i$ and the last switch of the next of the groups $Y_i$.

If input electric signals are applied between the first comb-shaped electrode and the counter electrode via the groups $X_i$ in turn, longitudinal waves are radiated along the direction vertical to the lower end surface of the piezoelectric substrate into the material in the form of a scanned ultrasound beam as a whole. The longitudinal waves are reflected at the object, and detected between the second comb-shaped electrode and the counter electrode by means of the groups $Y_i$ in turn in the form of a scanned electric signal as a whole.

According to another aspect of the present invention there is provided an ultrasound radiating and receiving device comprising a first piezoelectric substrate, a first interdigital arrangement of two comb-shaped electrodes, a second piezoelectric substrate, a second interdigital arrangement of two comb-shaped electrodes, and a counter electrode cemented between the first- and second piezoelectric substrates. The first interdigital arrangement is formed on a lower end surface of the first piezoelectric substrate. A lower end surface of the first interdigital arrangement is in contact with a surface-part of a material. The second interdigital arrangement is formed on an upper end surface of the second piezoelectric substrate.

If an input electric signal is applied between one of the two comb-shaped electrodes in the first interdigital arrangement and the counter electrode, a longitudinal wave is radiated into the material through the surface-part of the material along the direction vertical to the lower end surface of the first piezoelectric substrate. The longitudinal wave is reflected at an object located inside the material, and detected between one of the two comb-shaped electrodes in the second interdigital arrangement and the counter electrode as a delayed electric signal.

According to another aspect of the present invention there is provided an ultrasound radiating and receiving device, wherein the finger direction of the second interdigital arrangement is orthogonal to that of the first interdigital arrangement.

According to another aspect of the present invention there is provided an ultrasound radiating and receiving device, wherein the finger width in the one of the two comb-shaped electrodes in the first interdigital arrangement is wider than that in the other of the two comb-shaped electrodes in the first interdigital arrangement, and the finger width in the one of the two comb-shaped electrodes in the second interdigital arrangement is wider than that in the other of the two comb-shaped electrodes in the second interdigital arrangement.

According to another aspect of the present invention there is provided an ultrasound radiating and receiving device, wherein the ratio of the interdigital periodicity of the first interdigital arrangement to the thickness of the first piezoelectric substrate is smaller than four times the ratio of the longitudinal wave velocity in the material to the longitudinal wave velocity in the first piezoelectric substrate.

According to another aspect of the present invention there is provided an ultrasound radiating and receiving device, wherein increasing the number of electrode-finger pairs in the first interdigital arrangement makes the directionality of the longitudinal wave sharper under a condition that the total amount of all the finger-areas of the one of the two comb-shaped electrodes in the first interdigital arrangement is constant.

According to another aspect of the present invention there is provided a polymer film, with which the lower end surface of the first interdigital arrangement is coated.

According to another aspect of the present invention there are provided a first scanning unit composed of groups $X_i$ (i=11, ..., n) of switches corresponding to the electrode-fingers, respectively, of the one of the two comb-shaped electrodes in the first interdigital arrangement, and a second scanning unit composed of groups $Y_i$ (i=11, ..., n) of switches corresponding to the electrode-fingers, respectively, of the one of the two comb-shaped electrodes in the second interdigital arrangement. One and the next of the groups $X_i$ have common switches each other except the first switch of the one of the groups $X_i$ and the last switch of the next of the groups $X_i$. In the same way, one and the next of the groups $Y_i$ have common switches each other except the first switch of the one of the groups $Y_i$ and the last switch of the next of the groups $Y_i$.

If input electric signals are applied between the one of the two comb-shaped electrodes in the first interdigital arrangement and the counter electrode via the groups $X_i$ in turn, longitudinal waves are radiated along the direction vertical to the lower end surface of the first piezoelectric substrate into the material through the surface-part of the material in the form of a scanned ultrasound beam as a whole. The scanned ultrasound beam is reflected at the object, and detected between the one of the two comb-shaped electrodes in the second interdigital arrangement and the counter electrode by means of the groups $Y_i$ in turn as scanned electric signals. Thus, the upper surface-shape of the object is sensed from the scanned electric signals.

According to another aspect of the present invention there is provided an ultrasound radiating and receiving device comprising, a first piezoelectric substrate, a first comb-shaped electrode, a second piezoelectric substrate, a second comb-shaped electrode, and a counter electrode cemented between the first- and second piezoelectric substrates. The first comb-shaped electrode is formed on a lower end surface of the first piezoelectric substrate. A lower end surface of the first comb-shaped electrode is in contact with a surface-part of a material. The second comb-shaped electrode is formed on an upper end surface of the second piezoelectric substrate.

If an input electric signal is applied between the first comb-shaped electrode and the counter electrode, a longitudinal wave is radiated into the material through the surface-part of the material along the direction vertical to the lower end surface of the first piezoelectric substrate. The longitudinal wave is reflected at an object located inside the material, and detected between the second comb-shaped electrode and the counter electrode as a delayed electric signal.

According to another aspect of the present invention there is provided an ultrasound radiating and receiving device, wherein the finger direction of the second comb-shaped electrode is orthogonal to that of the first comb-shaped electrode.

According to another aspect of the present invention there is, provided an ultrasound radiating and receiving device, wherein the ratio of the interdigital periodicity of the first comb-shaped electrode to the thickness of the first piezoelectric substrate is smaller than four times the ratio of the longitudinal wave velocity in the material to the longitudinal wave velocity in the first piezoelectric substrate.

According to another aspect of the present invention there is provided an ultrasound radiating and receiving device, wherein increasing the number of electrode-finger pairs in the first comb-shaped electrode makes the directionality of the longitudinal wave sharper under a condition that the total amount of all the finger-areas of the first comb-shaped electrode is constant.

According to other aspect of the present invention there is provided a polymer film, with which the lower end surface of the first comb-shaped electrode is coated.

According to a further aspect of the present invention there are provided a first scanning unit composed of groups $X_i$ (i=1, 2, ... , n) of switches corresponding to the electrode-fingers, respectively, of the first comb-shaped electrode, and a second scanning unit composed of groups $Y_i$ (i=1, 2, ... , n) of switches corresponding to the electrode-fingers, respectively, of the second comb-shaped electrode. One and the next of the groups $X_i$ have common switches each other except the first switch of the one of the groups $X_i$ and the last switch of the next of the groups $X_i$. In the same way, one and the next of the groups $Y_i$ have common switches each other except the first switch of the one of the groups $Y_i$ and the last switch of the next of the groups $Y_i$.

If input electric signals are applied between the first comb-shaped electrode and the counter electrode via the groups $X_i$ in turn, longitudinal waves are radiated along the direction vertical to the lower end surface of the first piezoelectric substrate into the material through the surface-part of the material in the form of a scanned ultrasound beam as a whole. The scanned ultrasound beam is reflected at the object, and detected between the second comb-shaped electrode and the counter electrode by means of the groups $Y_i$ in turn as scanned electric signals. Thus, the upper surface-shape of the object is sensed from the scanned electric signals.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
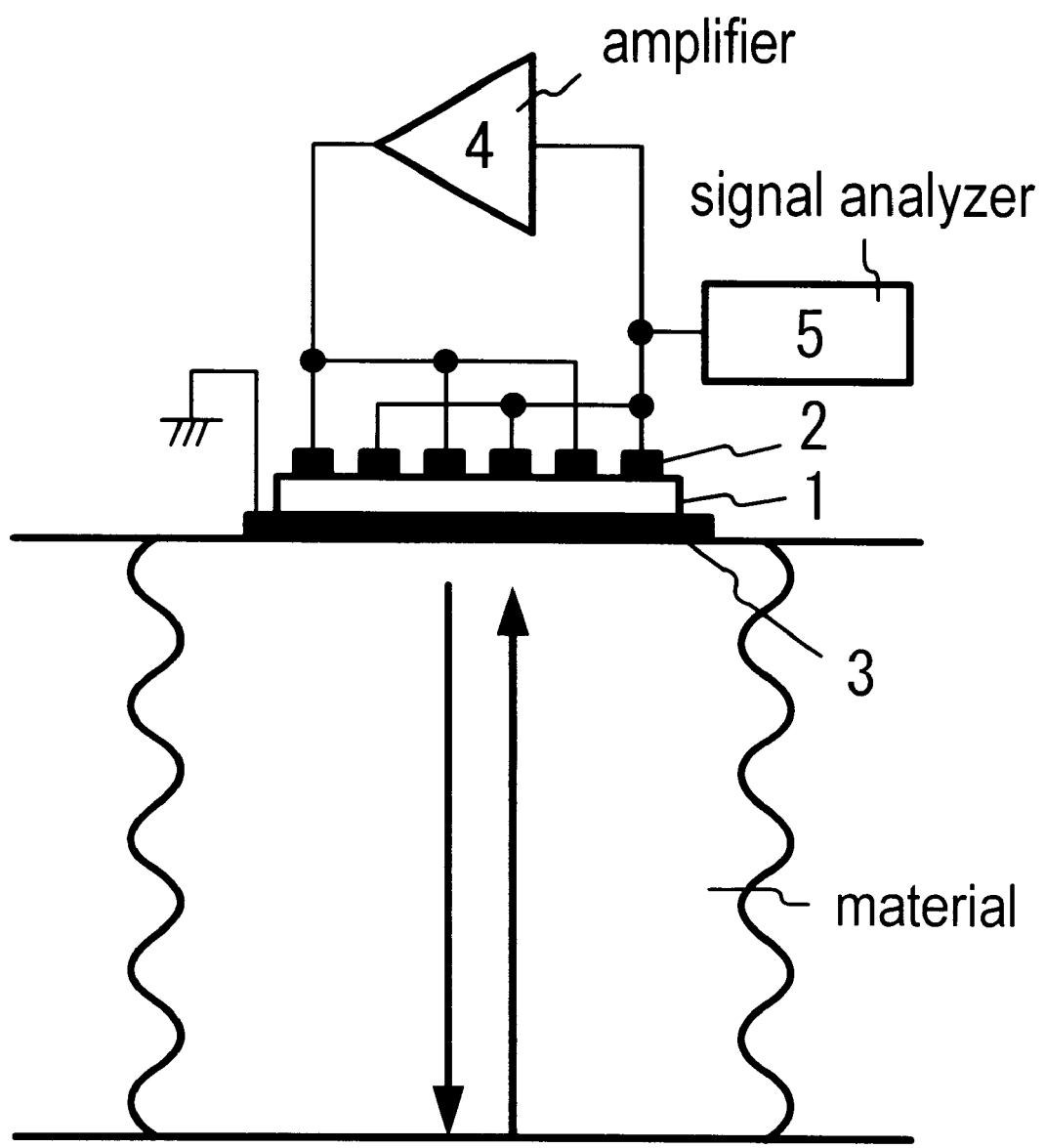
FIG. 1 shows a sectional view of an ultrasound radiating and receiving device according to a first embodiment of the present invention.

FIG. 1 shows a sectional view of an ultrasound radiating and receiving device according to a first embodiment of the present invention. The ultrasound radiating and receiving device comprises piezoelectric substrate 1, interdigital arrangement 2 of two comb-shaped electrodes (2A and 2B), counter electrode 3, amplifier 4, and signal analyzer 5.

Piezoelectric substrate 1 is made of a piezoelectric-ceramic plate with a thickness (T) of 500 μm, and the polarization axis thereof is parallel to the thickness direction thereof. Interdigital arrangement 2, made of an aluminum thin film, is formed on an upper end surface of piezoelectric substrate 1. Counter electrode 3, made of an aluminum thin film, is formed on a lower end surface of piezoelectric substrate 1. Thus, the ultrasound radiating and receiving device in FIG. 1 has a small size, which is very light in weight and has a simple structure. The lower end surface of counter electrode 3 is in contact with a surface-part of a material.

Figure 2:
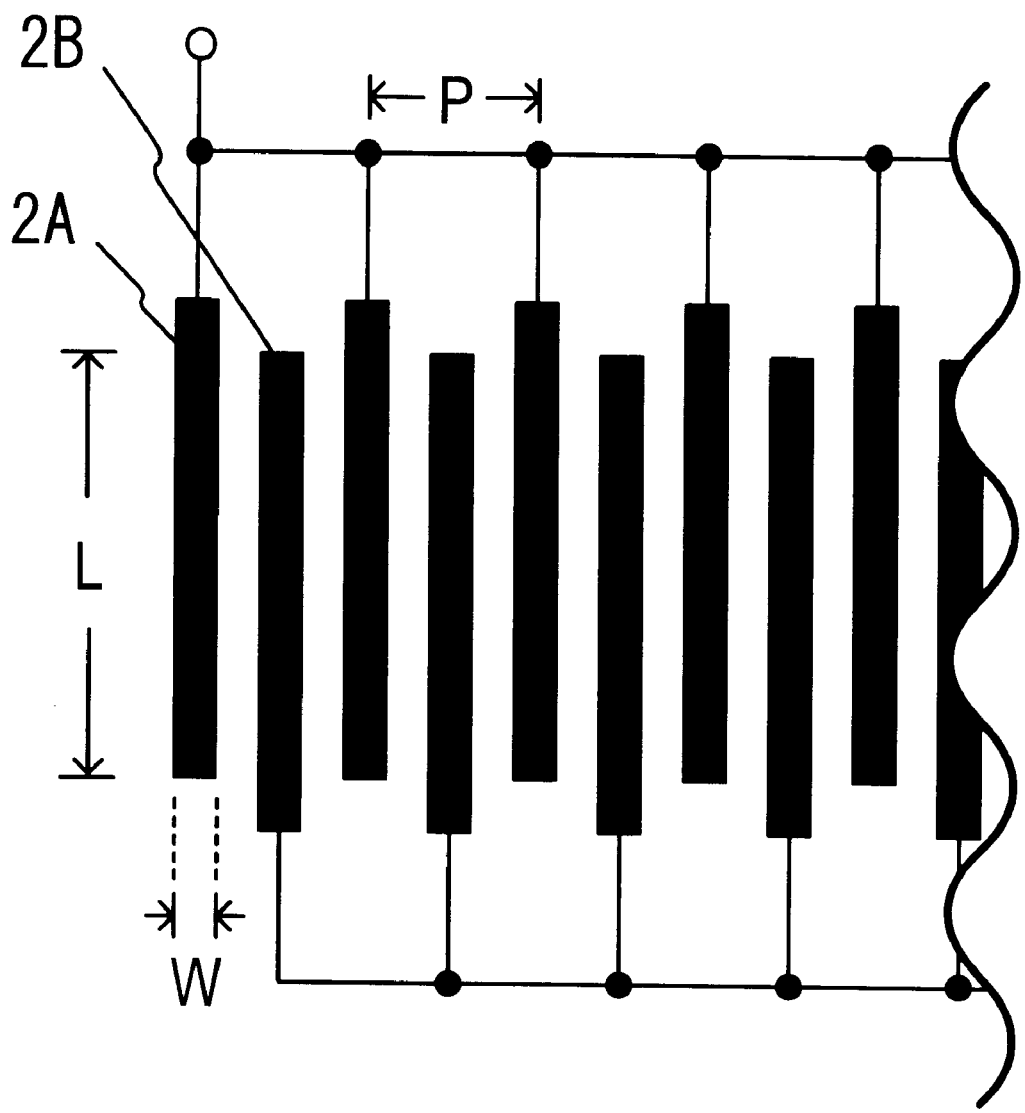
FIG. 2 shows a fragmentary top plan view of interdigital arrangement 2.

FIG. 2 shows a fragmentary top plan view of interdigital arrangement 2. Interdigital arrangement 2 has fifteen electrode-finger pairs, a finger-overlap length (L) of 5 mm, a finger width (W) of 75 μm, and an interdigital periodicity (P) of 300 μm. Interdigital arrangement 2 is composed of first comb-shaped electrode 2A and second comb-shaped electrode 2B. Amplifier 4 is connected between first comb-shaped electrode 2A and second comb-shaped electrode 2B in FIG. 1.

In the ultrasound radiating and receiving device in FIG. 1, if an input electric signal is applied between first comb-shaped electrode 2A and counter electrode 3, a longitudinal wave is radiated into the material through the surface-part of the material. If the material is water, the longitudinal wave velocity in water ($V_w$) is approximately 1,500 m/s. On the other hand, the longitudinal wave velocity in piezoelectric substrate 1 (V) is 4,500 m/s. Thus, the ratio of the $V_w$ value to the V value, that is 1,500/4,500, is approximately 0.333. As a result, the ratio of the interdigital periodicity (P) of interdigital arrangement 2 to the thickness (T) of piezoelectric substrate 1, that is 300/500, is 0.6, which is still smaller than four times the ratio of the $V_w$ value to the V value. Under such a condition of $P/T<4V_w/V$, the longitudinal wave along the direction vertical to the lower end surface of piezoelectric substrate 1 is effectively radiated into water. In the same way, the longitudinal wave is effectively radiated into, for example, a cellular tissue.

If the longitudinal wave is reflected at the opposite surface-part of the material, as shown in FIG. 1, or at an object located inside the material, a reflected longitudinal wave is detected between second comb-shaped electrode 2B and counter electrode 3 as a delayed electric signal, which is amplified via amplifier 4, as well as detected at signal analyzer 5. An amplified electric signal is supplied to first comb-shaped electrode 2A as the input electric signal again. Thus, supplying comb-shaped electrode 2A with the input electric signal via amplifier 4 causes a self-oscillation, and moreover causes the circuit construction simplified.

Figure 3:
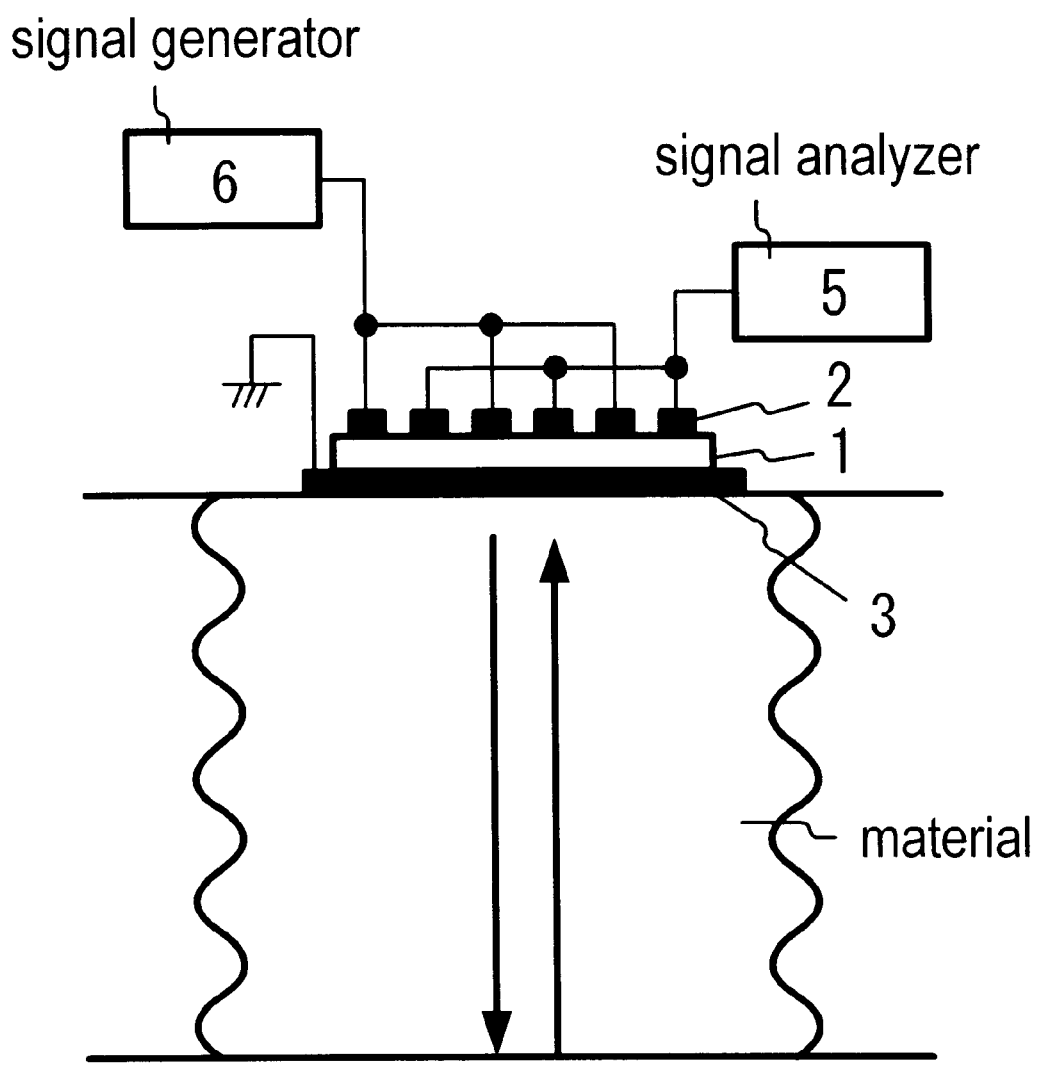
FIG. 3 shows a sectional view of an ultrasound radiating and receiving device according to a second embodiment of the present invention.

FIG. 3 shows a sectional view of an ultrasound radiating and receiving device according to a second embodiment of the present invention. The ultrasound radiating and receiving device has the same construction as FIG. 1 except for the absence of amplifier 4 and the presence of signal generator 6.

In the ultrasound radiating and receiving device in FIG. 3, if an input electric signal from signal generator 6 is applied between first comb-shaped electrode 2A and counter electrode 3, a longitudinal wave is radiated into the material through the surface-part of the material. If the longitudinal wave is reflected at the opposite surface-part of the material, as shown in FIG. 3, a reflected longitudinal wave is detected between second comb-shaped electrode 2B and counter electrode 3 as a delayed electric signal, which arrives at signal analyzer 5.

Figure 4:
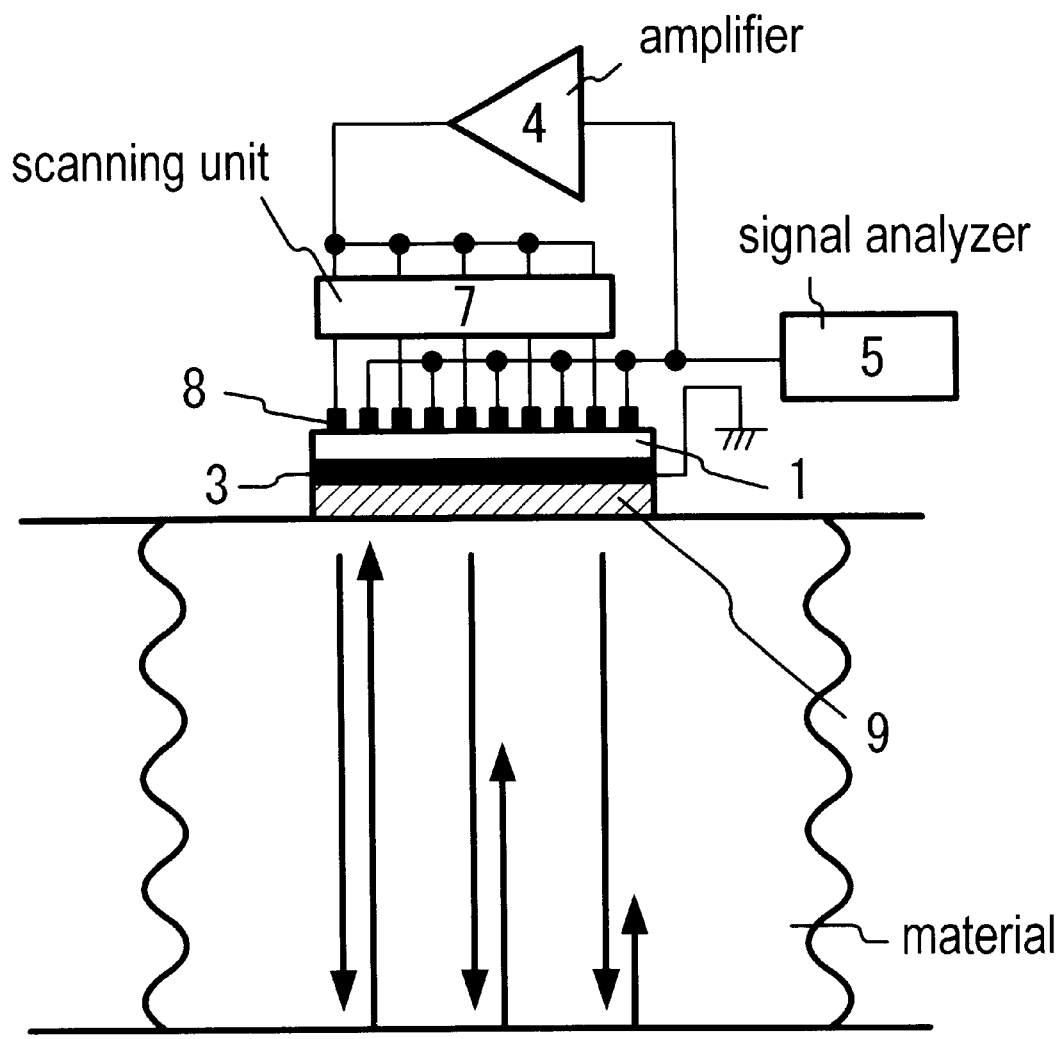
FIG. 4 shows a sectional view of an ultrasound radiating and receiving device according to a third embodiment of the present invention.

FIG. 4 shows a sectional view of an ultrasound radiating and receiving device according to a third embodiment of the present invention. The ultrasound radiating and receiving device comprises piezoelectric substrate 1, counter electrode 3, amplifier 4, signal analyzer 5, scanning unit 7, interdigital arrangement 8 of two comb-shaped electrodes (8A and 8B), and silicone rubber 9, with which the lower end surface of counter electrode 3 is coated. Silicone rubber 9 is in contact with a surface-part of a material.

Figure 5:
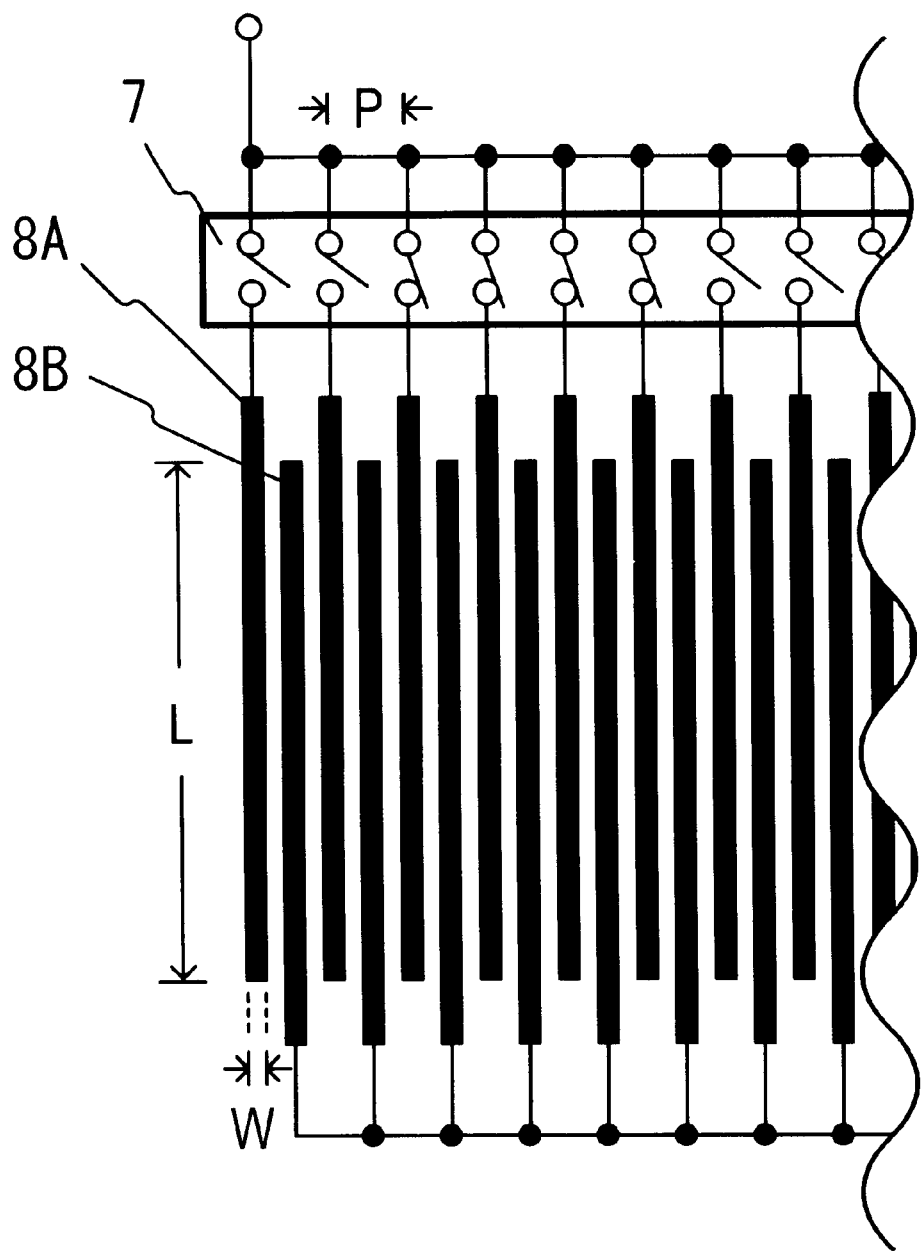
FIG. 5 shows a fragmentary top plan view of interdigital arrangement 8 connected with scanning unit 7.

FIG. 5 shows a fragmentary top plan view of interdigital arrangement 8 connected with scanning unit 7. Interdigital arrangement 8 has twenty electrode-finger pairs, a finger-overlap length (L) of 5 mm, a finger width (W) of 57 μm, and an interdigital periodicity (P) of 225 μm. Interdigital arrangement 8 is composed of first comb-shaped electrode 8A connected with amplifier 4 via scanning unit 7, and second comb-shaped electrode 8B connected with signal analyzer 5 in FIG. 4. Scanning unit 7 has twenty switches corresponding to the electrode-fingers of first comb-shaped electrode 8A, respectively. The twenty switches of scanning unit 7 form seventeen groups $X_i$ (i=1, 2, ..., 17), of which each has four switches. In this way, one and the next of the groups $X_i$ have three common switches each other except the first switch of the one of the groups $X_i$ and the last switch of the next of the groups $X_i$. For example, the groups $X_2$ and $X_3$ have three common switches each other except the first switch of the group $X_2$ and the last switch of the group $X_3$.

In the ultrasound radiating and receiving device in FIG. 4, if input electric signals are applied between counter electrode 3 and first comb-shaped electrode 8A via the groups $X_i$ in turn, seventeen longitudinal waves are radiated into the material in turn. In this way, the seventeen longitudinal waves are radiated in the form of a scanned ultrasound beam as a whole into the material through silicone rubber 9. When the material is water, the ratio of the $V_w$ value to the V value is approximately 0.333, as mentioned above. On the other hand, the ratio of the interdigital periodicity (P) of interdigital arrangement 8 to the thickness (T) of piezoelectric substrate 1, that is 225/500, is 0.45, which is still smaller than four times the ratio of the $V_w$ value to the V value. Under such a condition of $P/T<4V_w/V$, the scanned ultrasound beam along the direction vertical to the lower end surface of piezoelectric substrate 1 is effectively radiated into water through silicone rubber 9. In addition, the directionality of the scanned ultrasound beam is sharper than that of the longitudinal wave in FIG. 1. In other words, the smaller value P/T than $4V_w/V$, the sharper directionality.

If the scanned ultrasound beam is reflected at the opposite surface-part of the material, as shown in FIG. 4, a reflected ultrasound beam is detected between counter electrode 3 and second comb-shaped electrode 8B as a scanned electric signal, which is amplified via amplifier 4, as well as detected at signal analyzer 5. An amplified electric signal is supplied to first comb-shaped electrode 8A as the input electric signals again. Thus, supplying comb-shaped electrode 8A with the input electric signals via amplifier 4 causes a self-oscillation, and moreover causes the circuit construction simplified.

Figure 6:
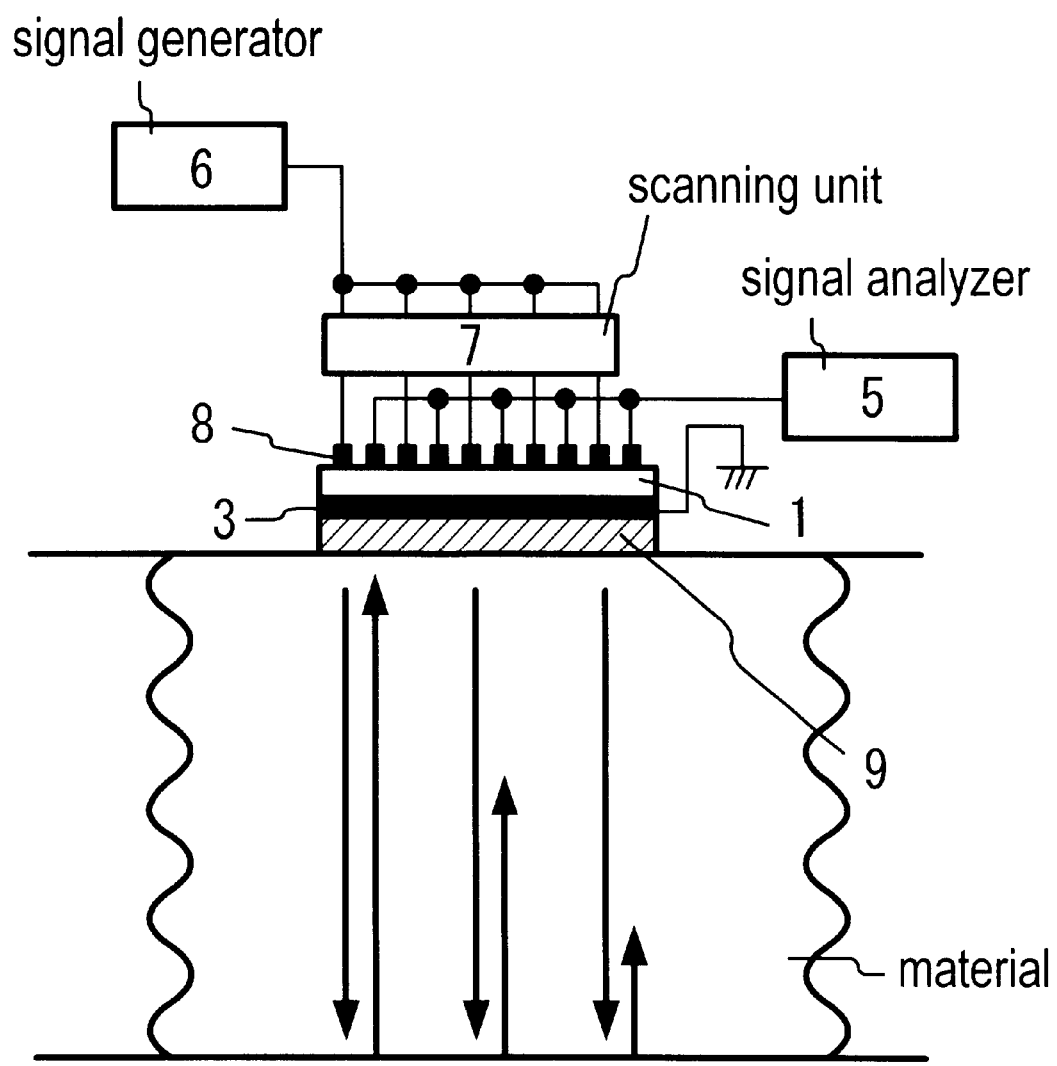
FIG. 6 shows a sectional view of an ultrasound radiating and receiving device according to a fourth embodiment of the present invention.

FIG. 6 shows a sectional view of an ultrasound radiating and receiving device according to a fourth embodiment of the present invention. The ultrasound radiating and receiving device has the same construction as FIG. 4 except for the absence of amplifier 4 and the presence of signal generator 6.

In the ultrasound radiating and receiving device in FIG. 6, if input electric signals from signal generator 6 are applied between counter electrode 3 and first comb-shaped electrode 8A via the groups $X_i$ in turn, seventeen longitudinal waves are radiated into the material in turn. In this way, the seventeen longitudinal waves are radiated in the form of a scanned ultrasound beam as a whole into the material through silicone rubber 9. If the scanned ultrasound beam is reflected at the opposite surface-part of the material, as shown in FIG. 6, a reflected ultrasound beam is detected as a scanned electric signal between counter electrode 3 and second comb-shaped electrode 8B. Then, the scanned electric signal arrives at signal analyzer 5.

Figure 7:
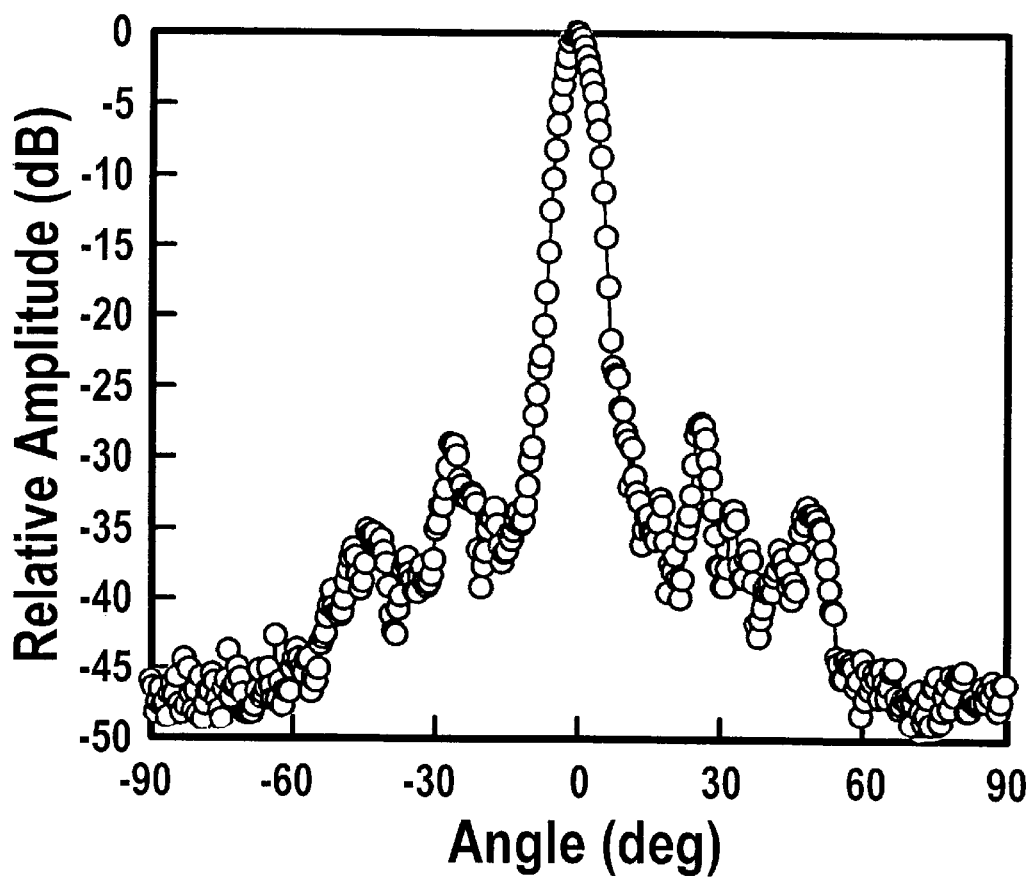
FIG. 7 shows a relationship between the relative amplitude and the radiation angle of one of the seventeen longitudinal waves into water from the ultrasound radiation device in FIG. 4.

FIG. 7 shows a relationship between the relative amplitude and the radiation angle of one of the seventeen longitudinal waves into water from the ultrasound radiation device in FIG. 4. It seems that there exists only the main lobe, because any grating lobe is suppressed. As a result, the use of interdigital arrangement 8 enables only a vertical radiation to the lower end surface of piezoelectric substrate 1 into water. Thus, the longitudinal waves are effectively radiated into, for example, a cellular tissue through a skin, along a vertical direction to the lower end surface of piezoelectric substrate 1.

Figure 8:
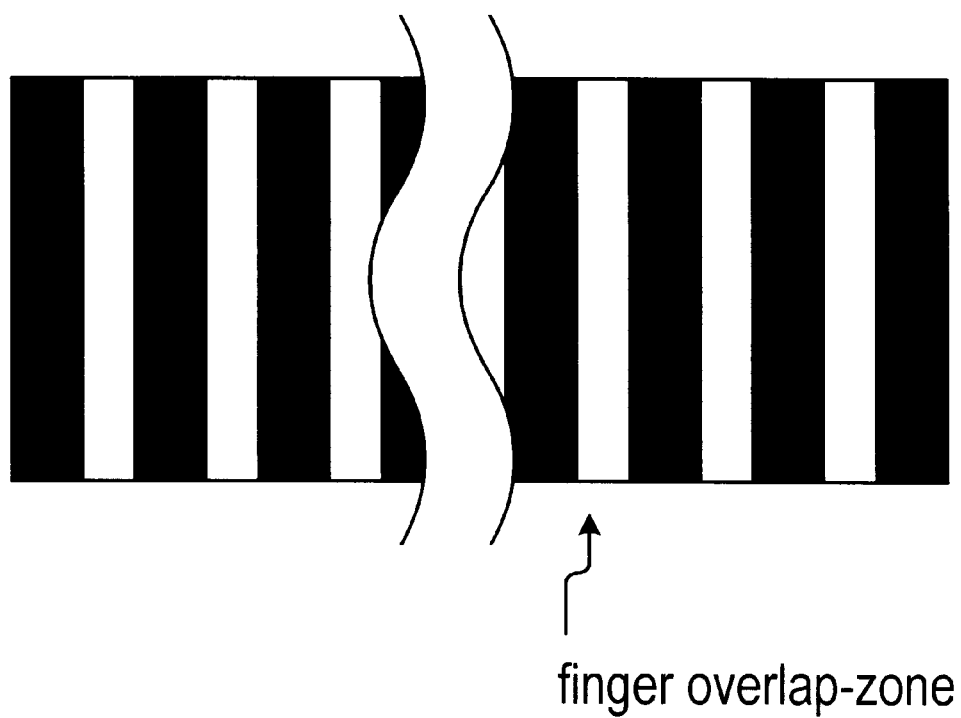
FIG. 8 shows a top plan view of the finger overlap-zone of interdigital arrangement 2.

FIG. 8 shows a top plan view of the finger overlap-zone of interdigital arrangement 2.

Figure 9:
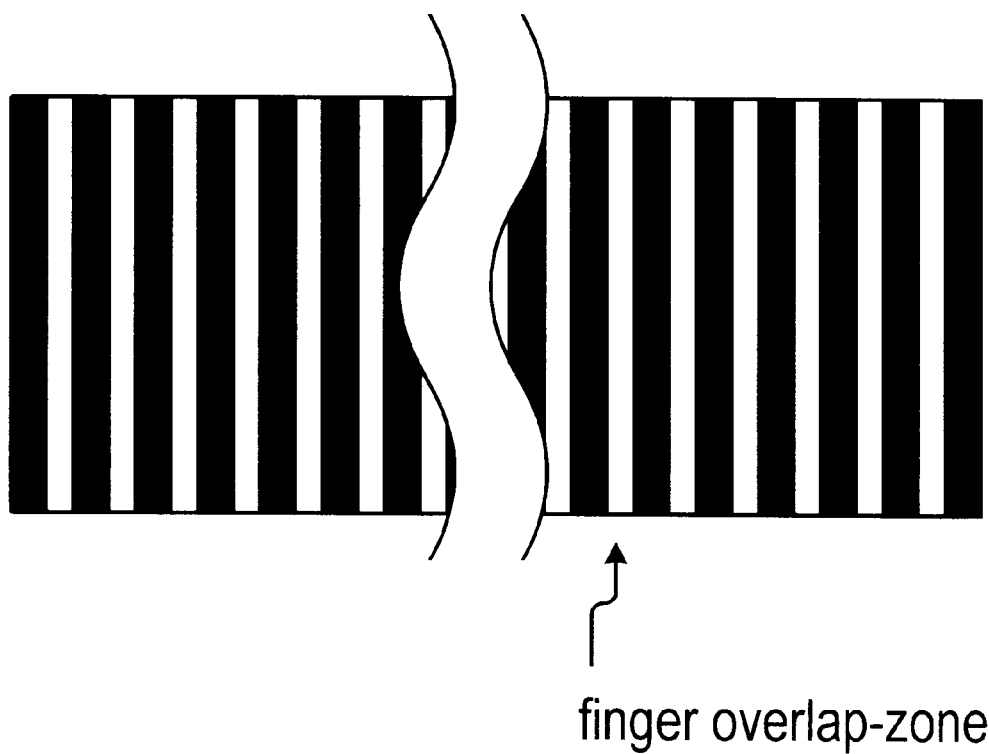
FIG. 9 shows a top plan view of the finger overlap-zone of interdigital arrangement 8.

FIG. 9 shows a top plan view of the finger overlap-zone of interdigital arrangement 8. The finger overlap-zone of interdigital arrangement 8 and that of interdigital arrangement 2 are the same in size. In addition, the total amount of all the finger-areas of comb-shaped electrode 8A is the same as that of comb-shaped electrode 2A.

A comparison between FIGS. 8 and 9 indicates that interdigital arrangement 8 and interdigital arrangement 2 are different from each other with respect to the number of electrode-finger pairs, the finger width (W), and the interdigital periodicity (P). Actually, the number of electrode-pairs in interdigital arrangement 8 is 4/3 times that in interdigital arrangement 2. At the same time, the interdigital periodicity (P) of interdigital arrangement 8 is approximately 3/4 times that of interdigital arrangement 2, and the finger width (W) of interdigital arrangement 8 is also 3/4 times that of interdigital arrangement 2. It is recognized that the use of interdigital arrangement 8 causes a sharper directionality of the longitudinal wave than interdigital arrangement 2. This means that increasing the number of electrode-finger pairs suppresses the grating lobes still more under a condition that the total amount of all the finger-areas of the first comb-shaped electrode is constant. As a result, the number of electrode-finger pairs has influence on the directionality of the longitudinal wave into a material under the condition that the total amount of all the finger-areas of the first comb-shaped electrode is constant.

Figure 10:
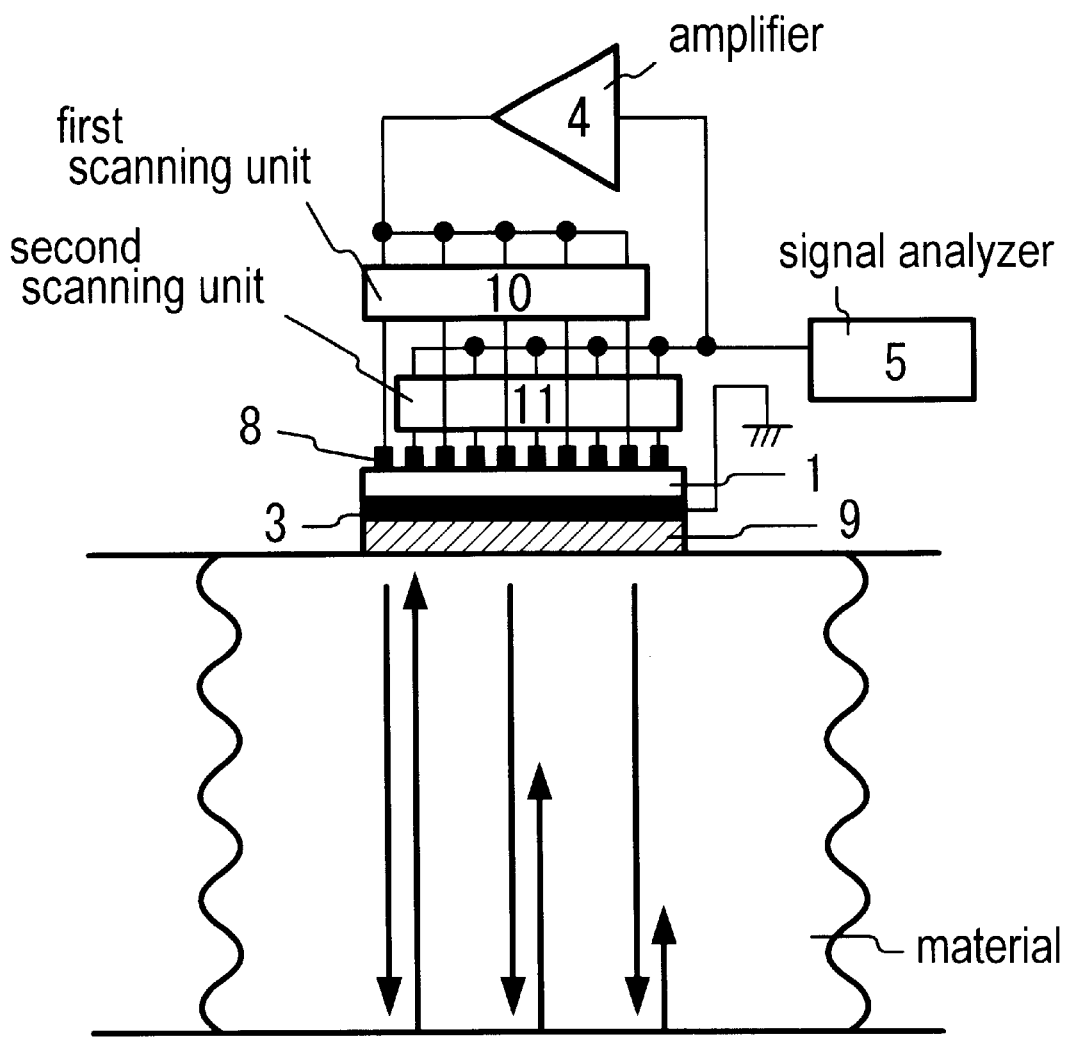
FIG. 10 shows a sectional view of an ultrasound radiating and receiving device according to a fifth embodiment of the present invention.

FIG. 10 shows a sectional view of an ultrasound radiating and receiving device according to a fifth embodiment of the present invention. The ultrasound radiating and receiving device has the same construction as FIG. 4 except for the absence of scanning unit 7, and the presence of first scanning unit 10 and second scanning unit 11.

Figure 11:
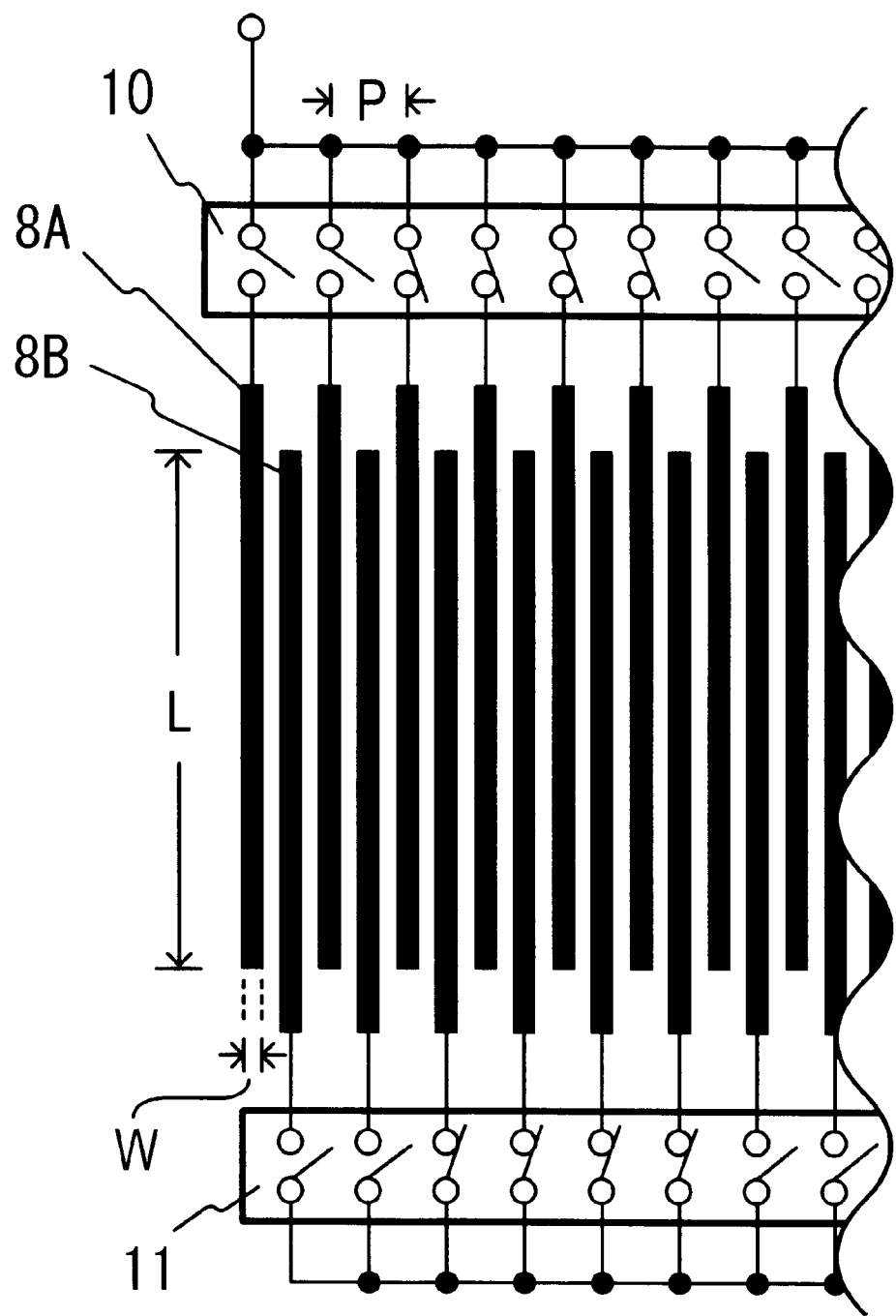
FIG. 11 shows fragmentary a top plan view of interdigital arrangement 8 connected with first scanning unit 10 and second scanning unit 11.

FIG. 11 shows fragmentary a top plan view of interdigital arrangement 8 connected with first scanning unit 10 and second scanning unit 11. First comb-shaped electrode 8A is connected with amplifier 4 via first scanning unit 10, and second comb-shaped electrode 8B is connected with signal analyzer 5 via second scanning unit 11 in FIG. 10. First scanning unit 10 has twenty switches corresponding to the electrode-fingers of first comb-shaped electrode 8A, respectively. In the same way, second scanning unit 11 has twenty switches corresponding to the electrode-fingers of second comb-shaped electrode 8B, respectively. The twenty switches of first scanning unit 10 form seventeen groups $X_i$ (i=1, 2, . . . , 17), of which each has four switches. In this way, one and the next of the groups $X_i$ have three common switches each other except the first switch of the one of the groups $X_i$ and the last switch of the next of the groups $X_i$. In the same way, the twenty switches of second scanning unit 11 form seventeen groups $Y_i$ (i=1, 2, . . . , 17) under a condition that each of the groups $Y_i$ has four switches. In this time, one and the next of the groups $Y_i$ have three common switches each other except the first switch of the one of the groups $Y_i$ and the last switch of the next of the groups $Y_i$.

In the ultrasound radiating and receiving device in FIG. 10, if input electric signals are applied between counter electrode 3 and first comb-shaped electrode 8A via the groups $X_i$ of first scanning unit 10 in turn, seventeen longitudinal waves are radiated in the form of a scanned ultrasound beam as a whole into the material through silicone rubber 9. When the material is water, the scanned ultrasound beam along the direction vertical to the lower end surface of piezoelectric substrate 1 is effectively radiated into water through silicone rubber 9 under the condition of $P/T<4V_w/V$.

If the seventeen longitudinal waves are reflected at the opposite surface-part of the material, as shown in FIG. 10, seventeen reflected longitudinal waves are detected as delayed electric signals between counter electrode 3 and second comb-shaped electrode 8B by means of the groups $Y_i$ in turn. In other words, a scanned electric signal is detected as a whole between counter electrode 3 and second comb-shaped electrode 8B by means of the groups $Y_i$ of second scanning unit 11. The scanned electric signal is amplified via amplifier 4, as well as detected at signal analyzer 5. An amplified electric signal is supplied to first comb-shaped electrode 8A as the input electric signals again. Thus, supplying comb-shaped electrode 8A with the input electric signals via amplifier 4 causes a self-oscillation, and moreover causes the circuit construction simplified.

Figure 12:
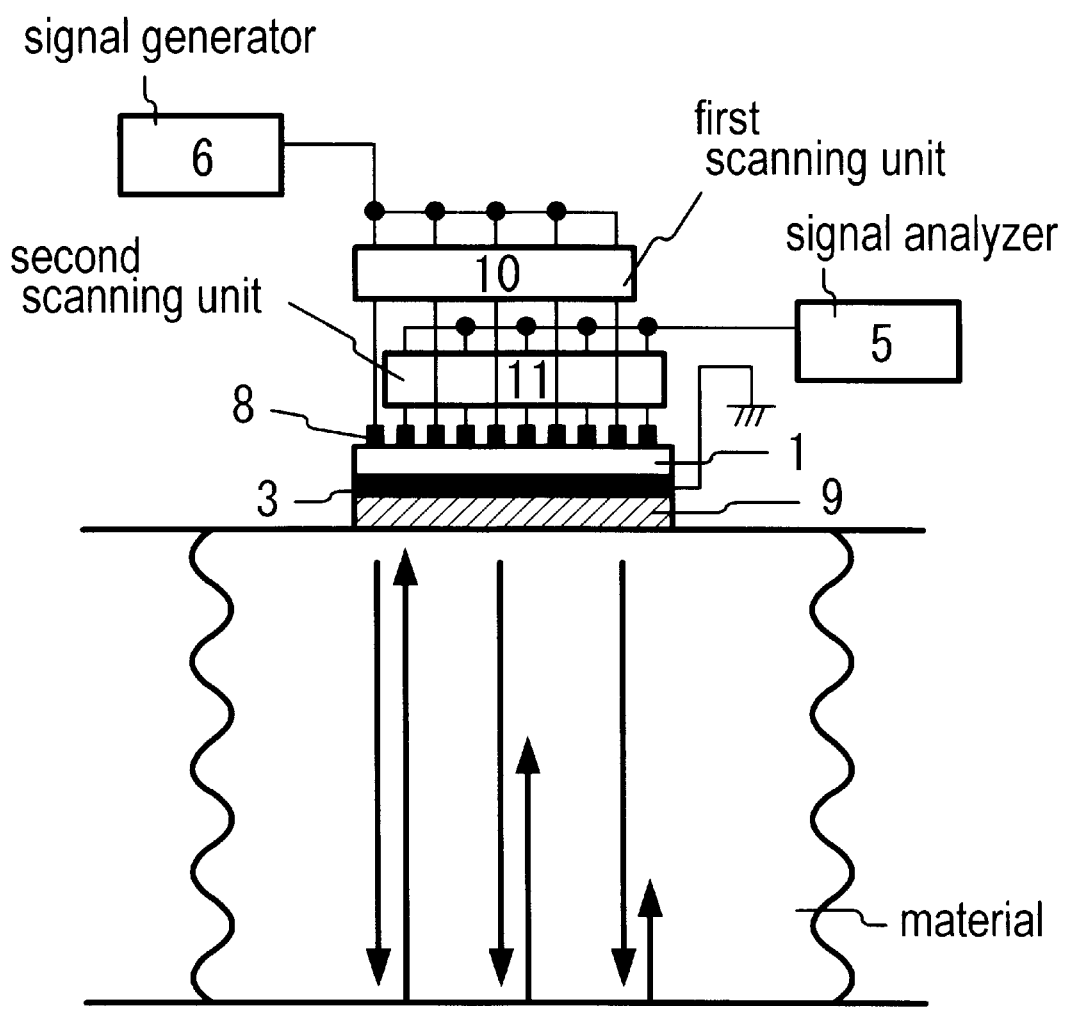
FIG. 12 shows a sectional view of an ultrasound radiating and receiving device according to a sixth embodiment of the present invention.

FIG. 12 shows a sectional view of an ultrasound radiating and receiving device according to a sixth embodiment of the present invention. The ultrasound radiating and receiving device has the same construction as FIG. 10 except for the absence of amplifier 4 and the presence of signal generator 6.

In the ultrasound radiating and receiving device in FIG. 12, if input electric signals from signal generator 6 are applied between counter electrode 3 and first comb-shaped electrode 8A via the groups $X_i$ of first scanning unit 10 in turn, seventeen longitudinal waves are radiated in the form of a scanned ultrasound beam as a whole into the material through silicone rubber 9. If the scanned ultrasound beam is reflected at the opposite surface-part of the material, as shown in FIG. 12, a scanned electric signal is detected between counter electrode 3 and second comb-shaped electrode 8B by means of the groups $Y_i$ of second scanning unit 11, and then the scanned electric signal arrives at signal analyzer 5.

Figure 13:
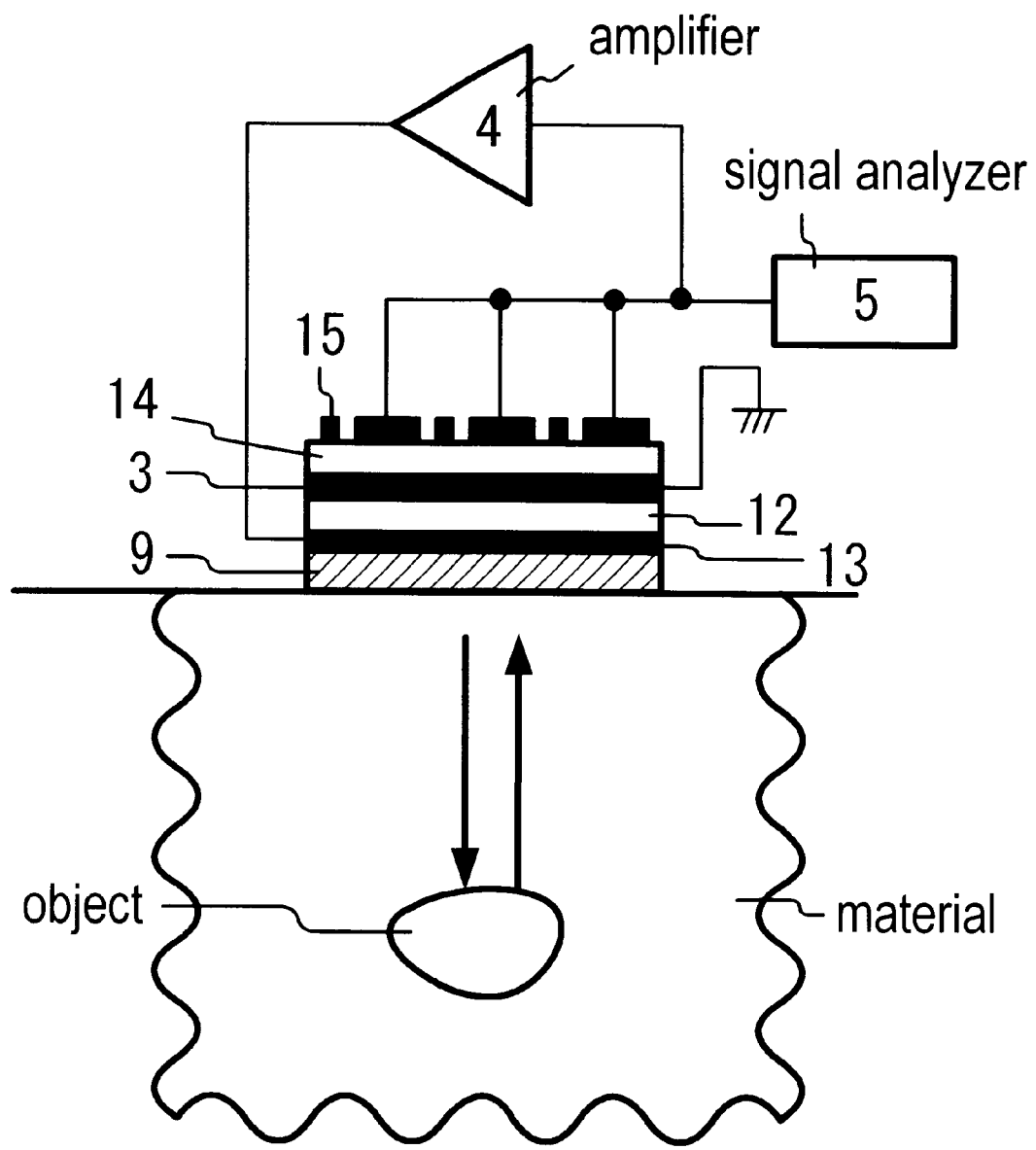
FIG. 13 shows a sectional view of an ultrasound radiating and receiving device according to a seventh embodiment of the present invention.

FIG. 13 shows a sectional view of an ultrasound radiating and receiving device according to a seventh embodiment of the present invention. The ultrasound radiating and receiving device comprises counter electrode 3, amplifier 4, signal analyzer 5, silicone rubber 9, first piezoelectric substrate 12, first interdigital arrangement 13 of two comb-shaped electrodes (13A and 13B), second piezoelectric substrate 14, and second interdigital arrangement 15 of two comb-shaped electrodes (15A and 15B). First interdigital arrangement 13, made of an aluminum thin film, is formed on a lower end surface of first piezoelectric substrate 12. Second interdigital arrangement 15, made of an aluminum thin film, is formed on an upper end surface of second piezoelectric substrate 14. Counter electrode 3 is cemented between first piezoelectric substrate 12 and second piezoelectric substrate 14, which are made of the same materials as piezoelectric substrate 1, and have the same sizes as piezoelectric substrate 1. The lower end surface of first interdigital arrangement 13 is coated with silicone rubber 9, which is in contact with a surface-part of a material.

Figure 14:
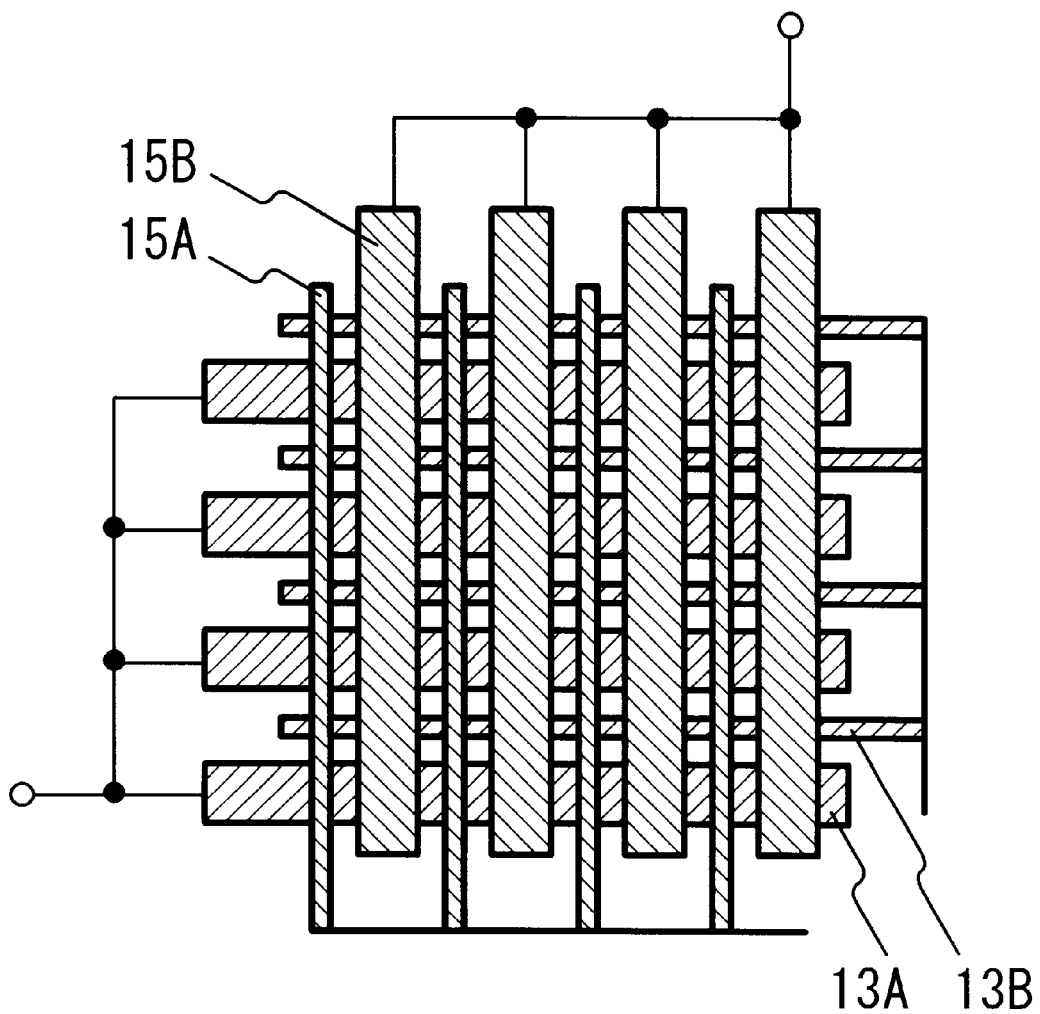
FIG. 14 shows a schematic illustration of first interdigital arrangement 13 and second interdigital arrangement 15.

FIG. 14 shows a schematic illustration of first interdigital arrangement 13 composed of first comb-shaped electrode 13A and second comb-shaped electrode 13B, and second interdigital arrangement 15 composed of first comb-shaped electrode 15A and second comb-shaped electrode 15B in the ultrasound radiating and receiving device in FIG. 13. The finger direction of first interdigital arrangement 13 is orthogonal to that of second interdigital arrangement 15. First interdigital arrangement 13 has twenty electrode-finger pairs, a finger-overlap length (L) of 5 mm, and an interdigital periodicity (P) of 225 $\mu$m. First comb-shaped electrode 13A has a finger width ($W_A$) of 45 $\mu$m, and second comb-shaped electrode 13B has a finger width ($W_B$) of 12 $\mu$m. Second interdigital arrangement 15 has the same construction pattern as first interdigital arrangement 13 except that first comb-shaped electrode 15A has a finger width ($W_A$) of 12 $\mu$m, and second comb-shaped electrode 15B has a finger width ($W_B$) of 45 $\mu$m.

In the ultrasound radiating and receiving device in FIG. 13, if an input electric signal is applied between first comb-shaped electrode 13A and counter electrode 3, a longitudinal wave along the direction vertical to the lower end surface of first piezoelectric substrate 12 is radiated into the material through silicone rubber 9. When the material is water, the condition of P/T <$4V_w$/V enables a radiation of the longitudinal wave along the direction vertical to the lower end surface of first piezoelectric substrate 12 into water. In addition, a condition of $W_A/W_B$ in first interdigital arrangement 13 makes the directionality of the longitudinal wave sharper.

If the longitudinal wave is reflected at an object located inside the material, as shown in FIG. 13, a reflected longitudinal wave is detected between second comb-shaped electrode 15B and counter electrode 3 as a delayed electric signal. In this time, the directionality of the reflected longitudinal wave is still sharper than that of the longitudinal wave radiated into the material, because the finger direction of first interdigital arrangement 13 is orthogonal to that of second interdigital arrangement 15.

The delayed electric signal detected between second comb-shaped electrode 15B and counter electrode 3 is amplified via amplifier 4, as well as detected at signal analyzer 5. An amplified electric signal is supplied to first comb-shaped electrode 13A as the input electric signal again. Thus, first comb-shaped electrode 13A, amplifier 4, and second comb-shaped electrode 15B form a self-oscillation type of delay-line oscillator.

Figure 15:
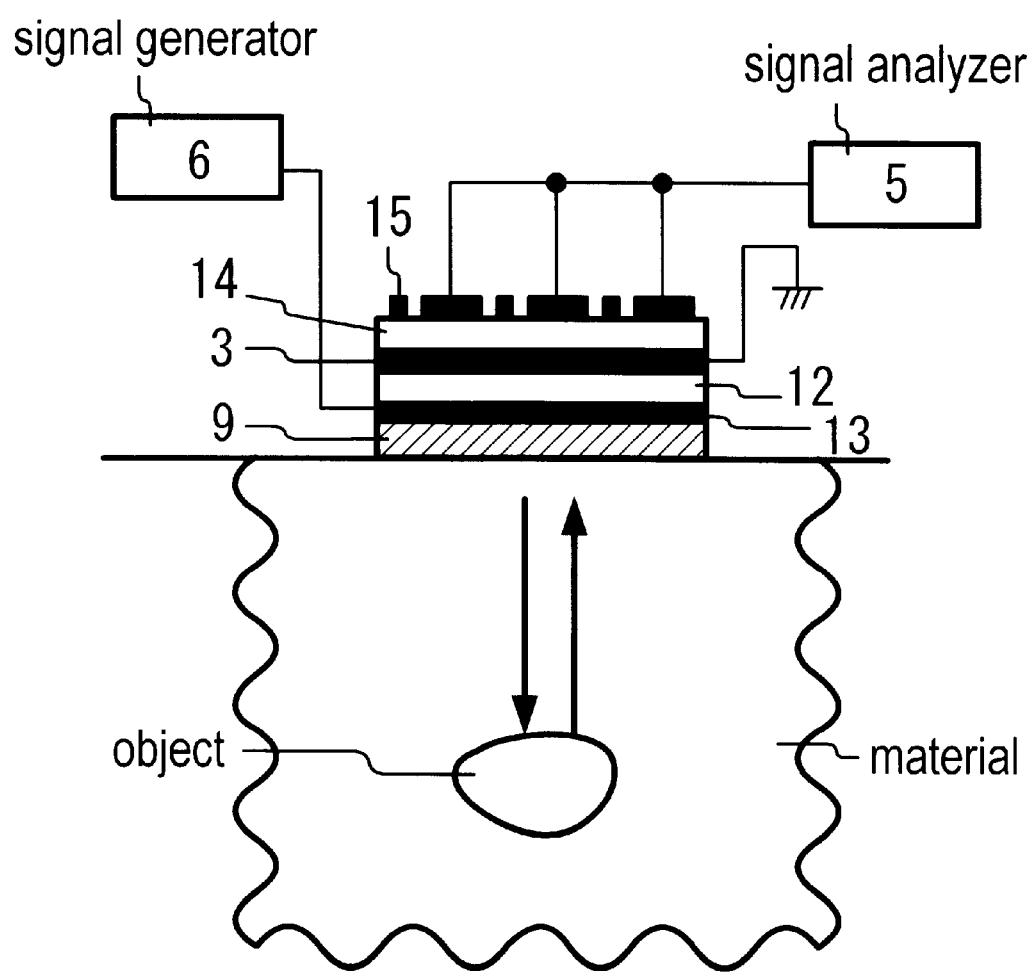
FIG. 15 shows a sectional view of an ultrasound radiating and receiving device according to an eighth embodiment of the present invention.

FIG. 15 shows a sectional view of an ultrasound radiating and receiving device according to an eighth embodiment of the present invention. The ultrasound radiating and receiving device has the same construction as FIG. 13 except for the absence of amplifier 4 and the presence of signal generator 6.

In the ultrasound radiating and receiving device in FIG. 15, if an input electric signal from signal generator 6 is applied between first comb-shaped electrode 13A and counter electrode 3, a longitudinal wave along the direction vertical to the lower end surface of first piezoelectric substrate 12 is radiated into the material through silicone rubber 9. If the longitudinal wave is reflected at an object located inside the material, as shown in FIG. 15, a reflected longitudinal wave is detected between second comb-shaped electrode 15B and counter electrode 3 as a delayed electric signal, which arrives at signal analyzer 5.

Figure 16:
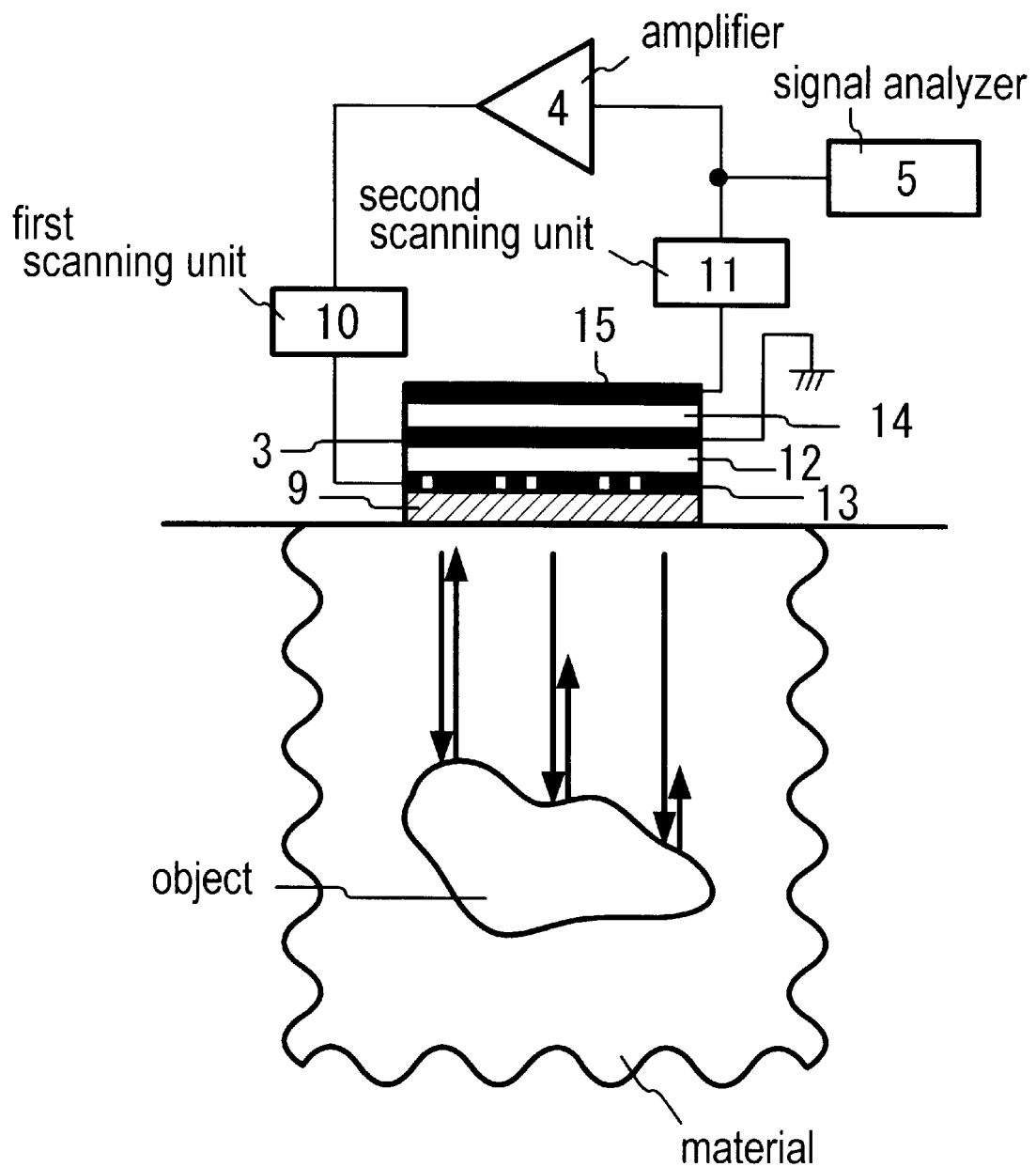
FIG. 16 shows a sectional view of an ultrasound radiating and receiving device according to a ninth embodiment of the present invention.

FIG. 16 shows a sectional view of an ultrasound radiating and receiving device according to a ninth embodiment of the present invention. The ultrasound radiating and receiving device has the same construction as FIG. 13 except for the presence of first scanning unit 10 and second scanning unit 11.

Figure 17:
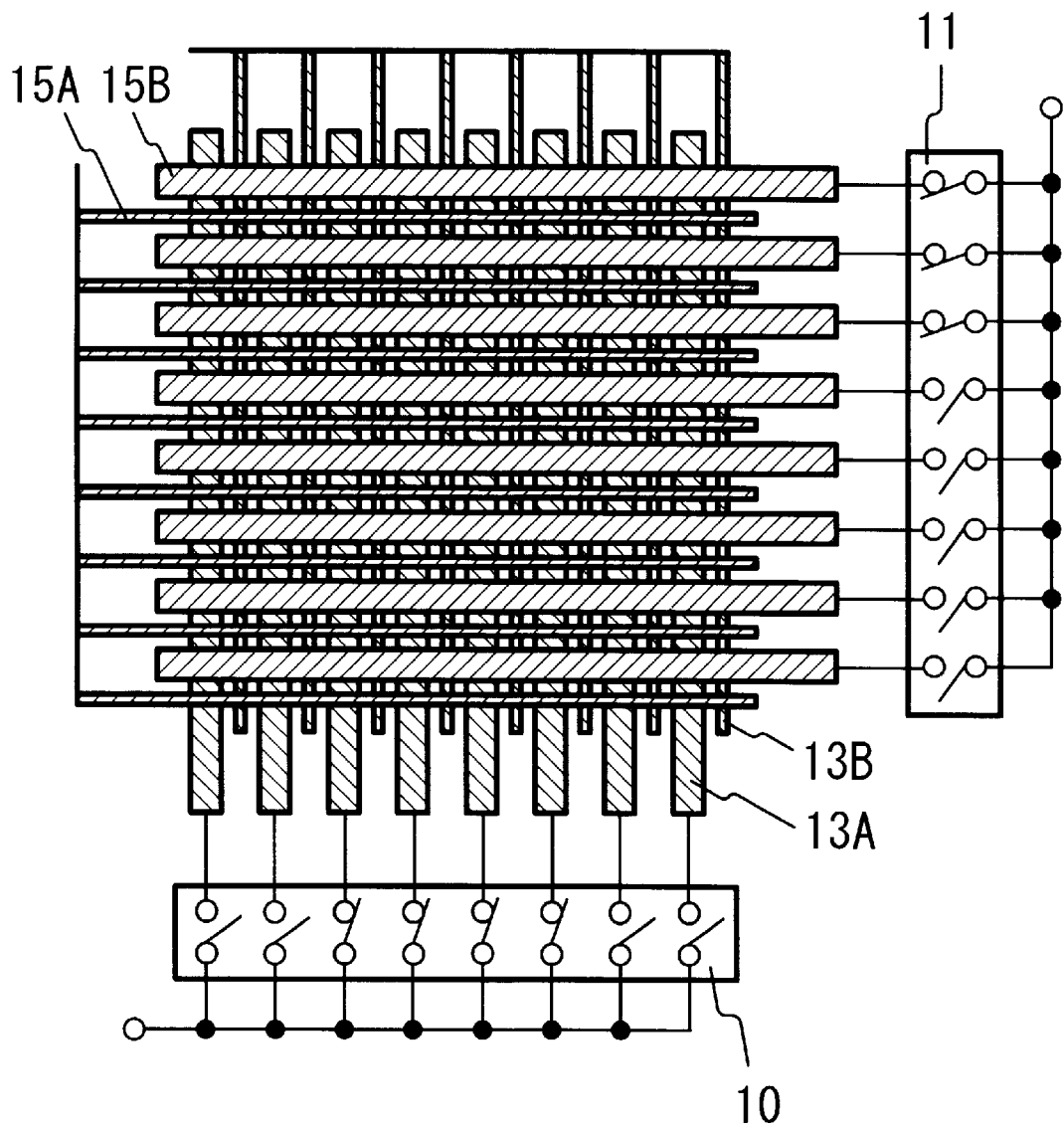
FIG. 17 shows a schematic illustration of first interdigital arrangement 13 and second interdigital arrangement 15.

FIG. 17 shows a schematic illustration of first interdigital arrangement 13 connected with first scanning unit 10, and second interdigital arrangement 15 connected with second scanning unit 11. First interdigital arrangement 13 is connected with amplifier 4 via first scanning unit 10, and second interdigital arrangement 15 is connected with signal analyzer 5 via second scanning unit 11 in FIG. 16. The electrode-fingers of first comb-shaped electrode 13A correspond with the twenty switches of first scanning unit 10, respectively. In the same way, the electrode-fingers of second comb-shaped electrode 15B correspond with the twenty switches of second scanning unit 11, respectively. The twenty switches of first scanning unit 10 form seventeen groups $X_i$ (i=1, 2, . . . , 17), of which each has four switches. In this way, one and the next of the groups $X_i$ have three common switches each other except the first switch of the one of the groups $X_i$ and the last switch of the next of the groups $X_i$. On the other hand, the twenty switches of second scanning unit 11 form eighteen groups $Y_i$ (i=1, 2, . . . , 18) under a condition that each of the groups $Y_i$ has three switches. In this time, one and the next of the groups $Y_i$ have two common switches each other except the first switch of the one of the groups $Y_i$ and the last switch of the next of the groups $Y_i$.

In the ultrasound radiating and receiving device in FIG. 16, if input electric signals are applied between counter electrode 3 and first comb-shaped electrode 13A via the groups $X_i$ in turn, seventeen longitudinal waves along the direction vertical to the lower end surface of first piezoelectric substrate 12 are radiated into the material in turn. In this way, the seventeen longitudinal waves are radiated in the form of a scanned ultrasound beam as a whole into the material through silicone rubber 9. When the material is water, the condition of P/T<$4V_w$/V enables a radiation of the scanned ultrasound beam along the direction vertical to the lower end surface of first piezoelectric substrate 12 into water.

If the scanned ultrasound beam is reflected at an object located inside the material, as shown in FIG. 16, a reflected and scanned ultrasound beam is detected as a scanned electric signal between counter electrode 3 and second comb-shaped electrode 15B by means of each of the groups $Y_i$. In other words, eighteen reflected and scanned ultrasound beams are detected as eighteen scanned electric signals between counter electrode 3 and second comb-shaped electrode 15B by means of the eighteen groups $Y_i$ in turn. As a result, the upper-surface shape of the object is imaged from the scanned electric signals at signal analyzer 5.

On the other hand, the scanned electric signals are amplified via amplifier 4, as well as detected at signal analyzer 5. Thus, amplified electric signals are supplied to first comb-shaped electrode 13A as the input electric signals again. As a result, first comb-shaped electrode 13A, amplifier 4, and second comb-shaped electrode 15B form a self-oscillation type of delay-line oscillator.

Figure 18:
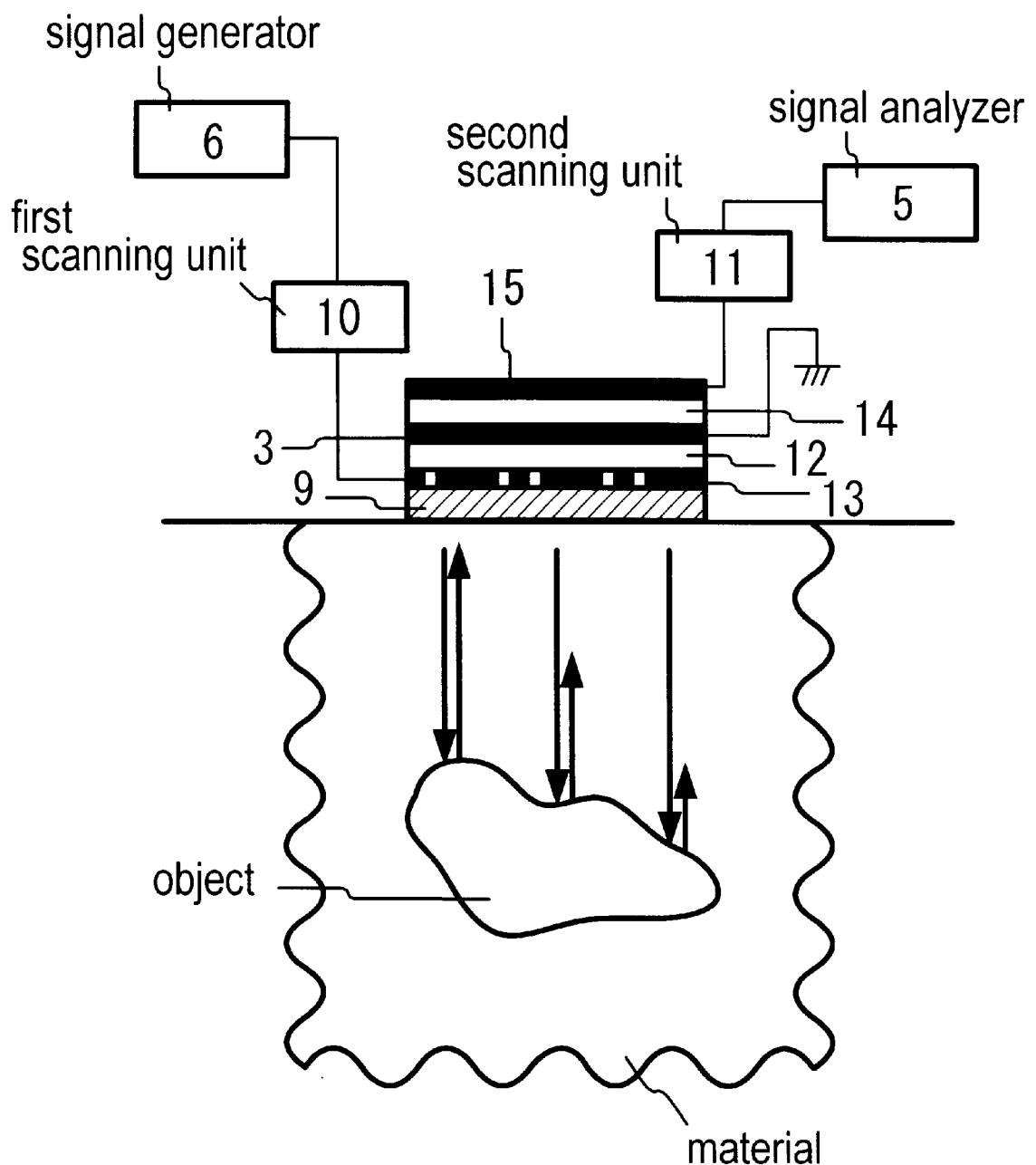
FIG. 18 shows a sectional view of an ultrasound radiating and receiving device according to a tenth embodiment of the present invention.

FIG. 18 shows a sectional view of an ultrasound radiating and receiving device according to a tenth embodiment of the present invention. The ultrasound radiating and receiving device has the same construction as FIG. 16 except for the absence of amplifier 4 and the presence of signal generator 6.

In the ultrasound radiating and receiving device in FIG. 18, if input electric signals from signal generator 6 are applied between counter electrode 3 and first comb-shaped electrode 13A via the groups $X_i$ in turn, seventeen longitudinal waves along the direction vertical to the lower end surface of first piezoelectric substrate 12 are radiated into the material in turn. In this way, the seventeen longitudinal waves are radiated in the form of a scanned ultrasound beam as a whole into the material through silicone rubber 9. If the scanned ultrasound beam is reflected at an object located inside the material, as shown in FIG. 18, a reflected and scanned ultrasound beam is detected as a scanned electric signal between counter electrode 3 and second comb-shaped electrode 15B by means of each of the groups $Y_i$. In other words, eighteen reflected and scanned ultrasound beams are detected as eighteen scanned electric signals between counter electrode 3 and second comb-shaped electrode 15B by means of the eighteen groups Y in turn. And then, the scanned electric signals arrive at signal analyzer 5. As a result, the upper-surface shape of the object is imaged from the scanned electric signals.

Figure 19:
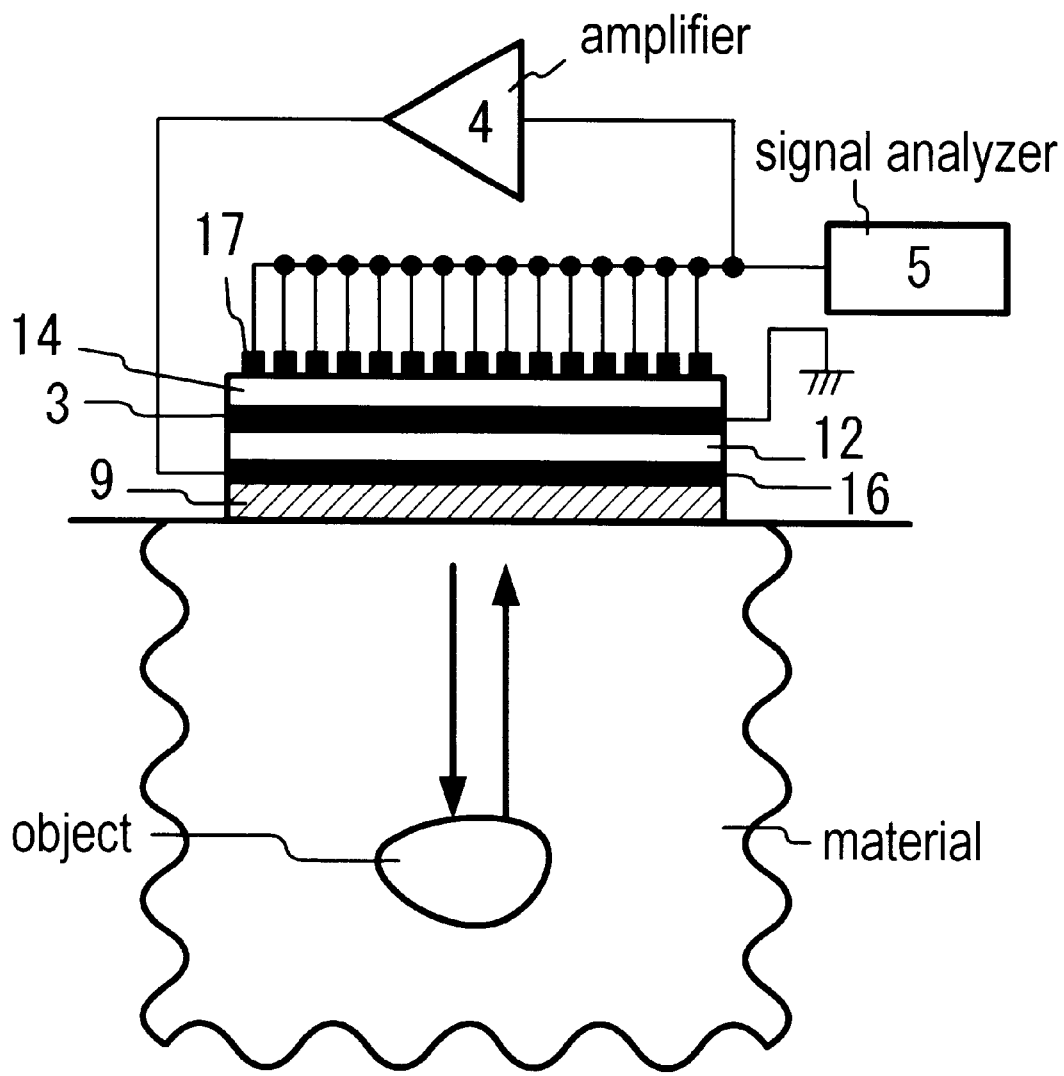
FIG. 19 shows a sectional view of an ultrasound radiating and receiving device according to an eleventh embodiment of the present invention.

FIG. 19 shows a sectional view of an ultrasound radiating and receiving device according to an eleventh embodiment of the present invention. The ultrasound radiating and receiving device has the same construction as FIG. 13 except for the presence of first comb-shaped electrode 16 and second comb-shaped electrode 17 in place of first interdigital arrangement 13 and second interdigital arrangement 15, respectively.

Figure 20:
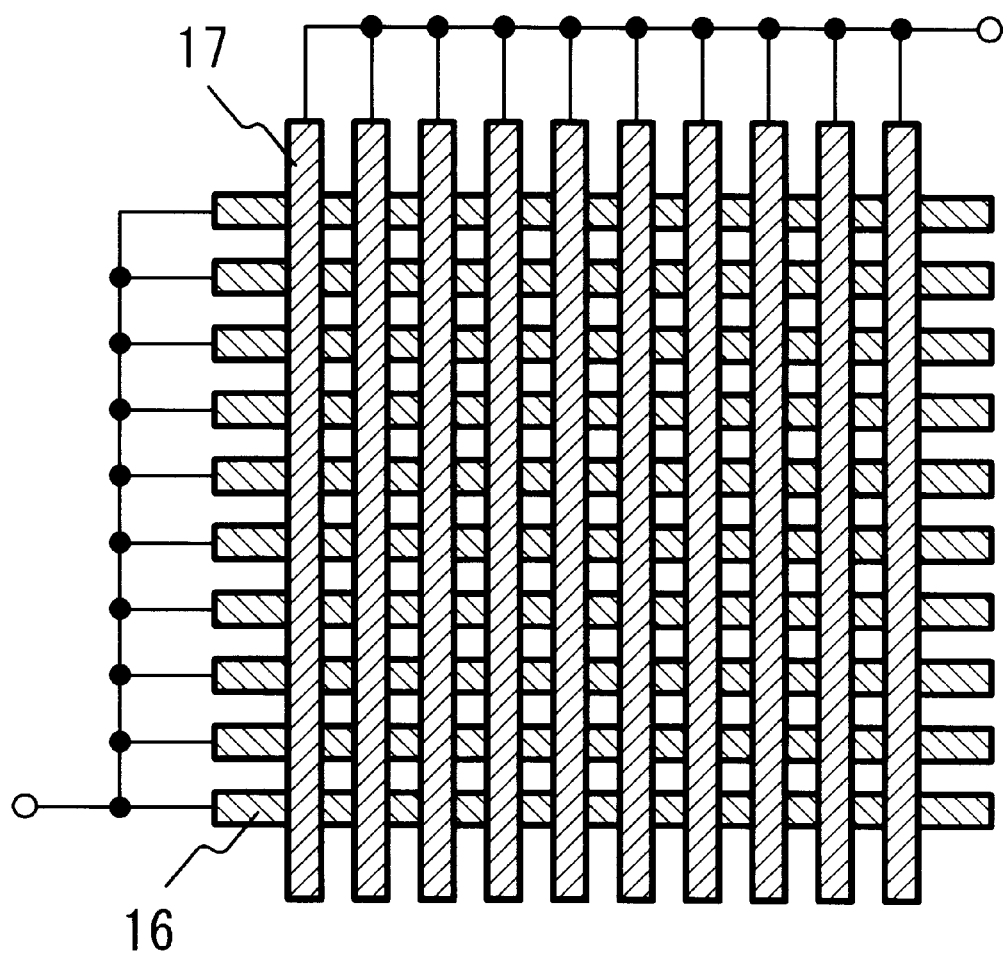
FIG. 20 shows a schematic illustration of first comb-shaped electrode 16 and second comb-shaped electrode 17.

FIG. 20 shows a schematic illustration of first comb-shaped electrode 16 and second comb-shaped electrode 17. First comb-shaped electrode 16 has forty electrode-fingers, a finger-overlap length (L) of 5 mm, a finger width (W) of 175 µm, and an interdigital periodicity (P) of 225 µm. Second comb-shaped electrode 17 has the same construction pattern as first comb-shaped electrode 16, of which the finger direction is orthogonal to that of second comb-shaped electrode 17.

In the ultrasound radiating and receiving device in FIG. 19, if an input electric signal is applied between first comb-shaped electrode 16 and counter electrode 3, a longitudinal wave along the direction vertical to the lower end surface of first piezoelectric substrate 12 is radiated into the material through silicone rubber 9. When the material is water, the condition of $P/T<4V_w/V$ enables a radiation of the longitudinal wave along the direction vertical to the lower end surface of first piezoelectric substrate 12 into water.

If the longitudinal wave is reflected at an object located inside the material, as shown in FIG. 19, a reflected longitudinal wave is detected between second comb-shaped electrode 17 and counter electrode 3 as a delayed electric signal. In this time, the directionality of the reflected longitudinal wave is still sharper than that of the longitudinal wave radiated into the material, because the finger direction of first comb-shaped electrode 16 is orthogonal to that of second comb-shaped electrode 17. In addition, first comb-shaped electrode 16, amplifier 4, and second comb-shaped electrode 17 form a self-oscillation type of delay-line oscillator.

Figure 21:
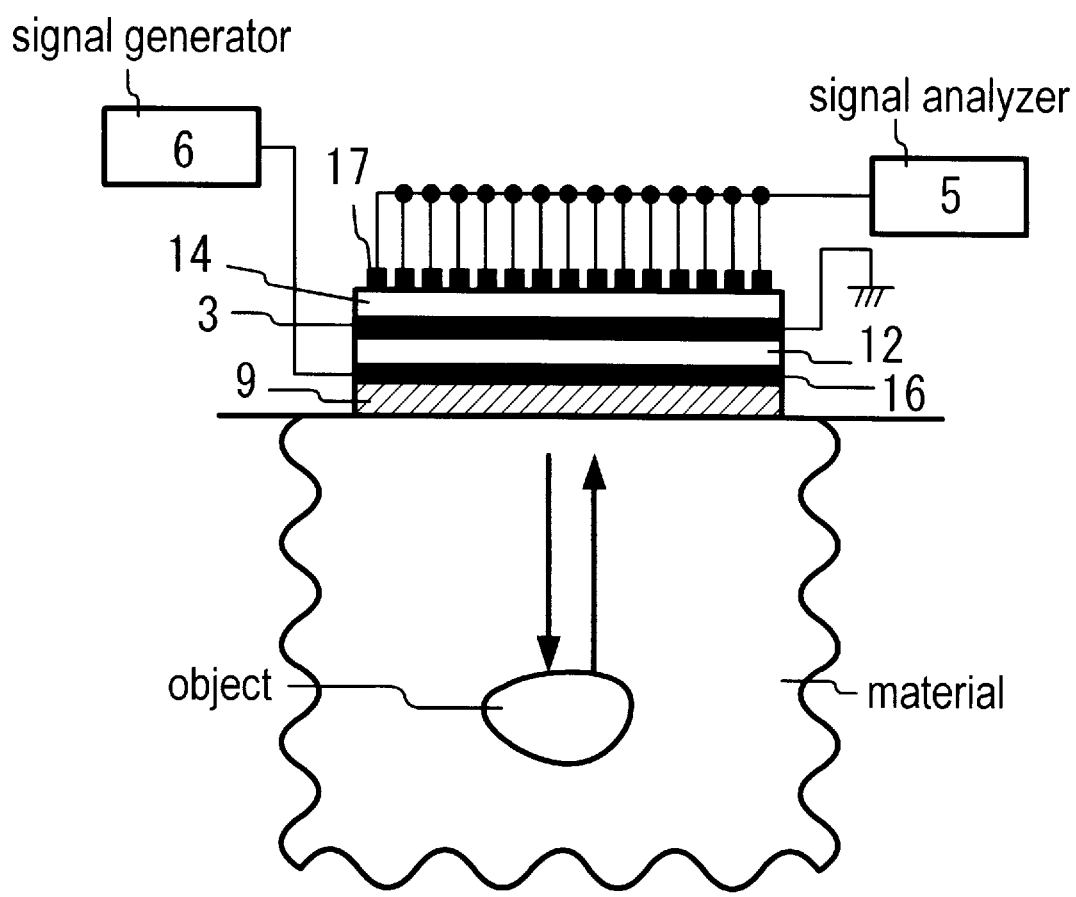
FIG. 21 shows a sectional view of an ultrasound radiating and receiving device according to a twelfth embodiment of the present invention.

FIG. 21 shows a sectional view of an ultrasound radiating and receiving device according to a twelfth embodiment of the present invention. The ultrasound radiating and receiving device has the same construction as FIG. 19 except for the absence of amplifier 4 and the presence of signal generator 6.

In the ultrasound radiating and receiving device in FIG. 21, if an input electric signal from signal generator 6 is applied between first comb-shaped electrode 16 and counter electrode 3, a longitudinal wave along the direction vertical to the lower end surface of first piezoelectric substrate 12 is radiated into the material through silicone rubber 9. If the longitudinal wave is reflected at an object located inside the material, as shown in FIG. 21, a reflected longitudinal wave is detected between second comb-shaped electrode 17 and counter electrode 3 as a delayed electric signal, which arrives at signal analyzer 5.

Figure 22:
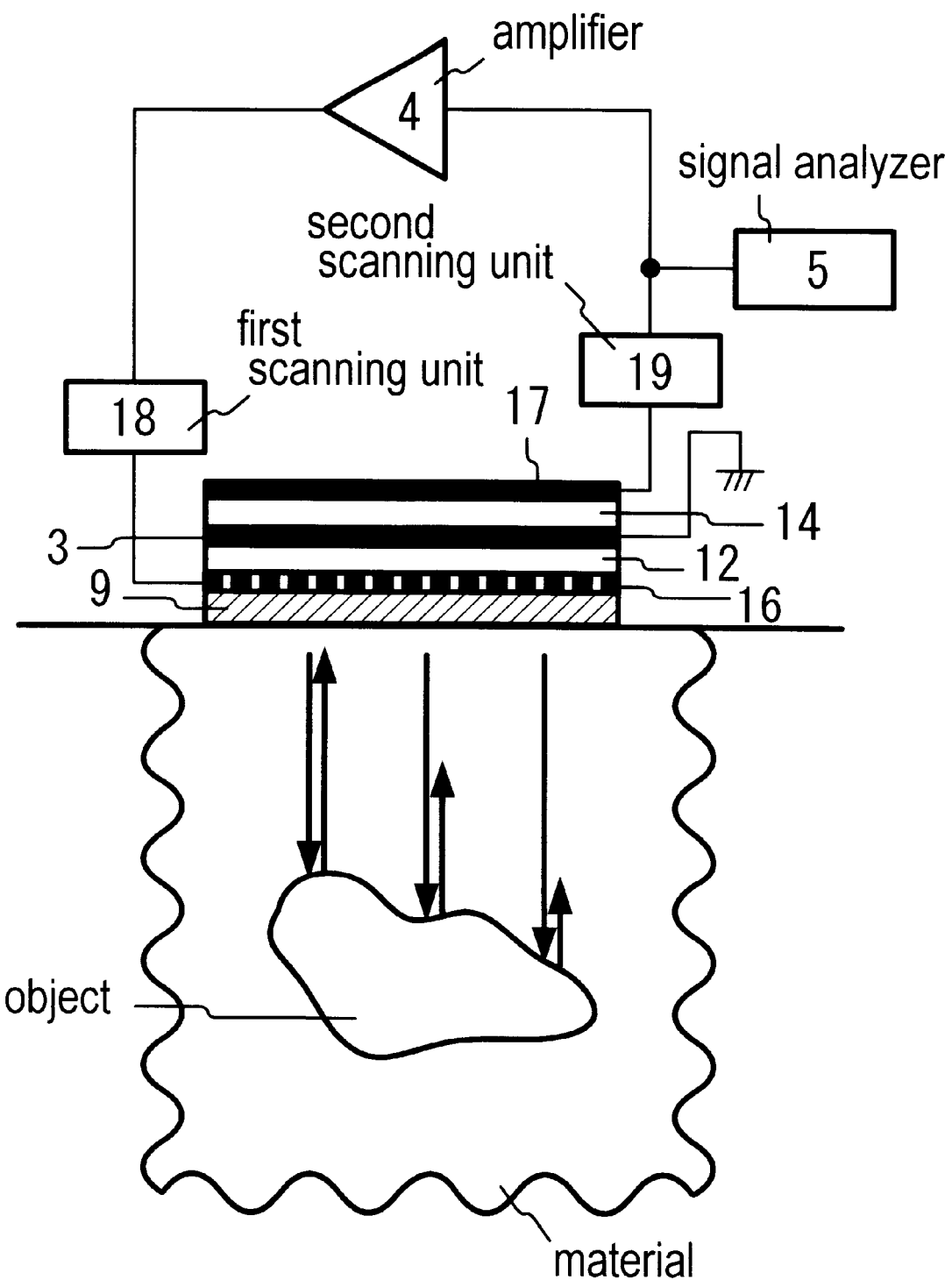
FIG. 22 shows a sectional view of an ultrasound radiating and receiving device according to a thirteenth embodiment of the present invention.

FIG. 22 shows a sectional view of an ultrasound radiating and receiving device according to a thirteenth embodiment of the present invention. The ultrasound radiating and receiving device has the same construction as FIG. 19 except for the presence of first scanning unit 18 and second scanning unit 19.

Figure 23:
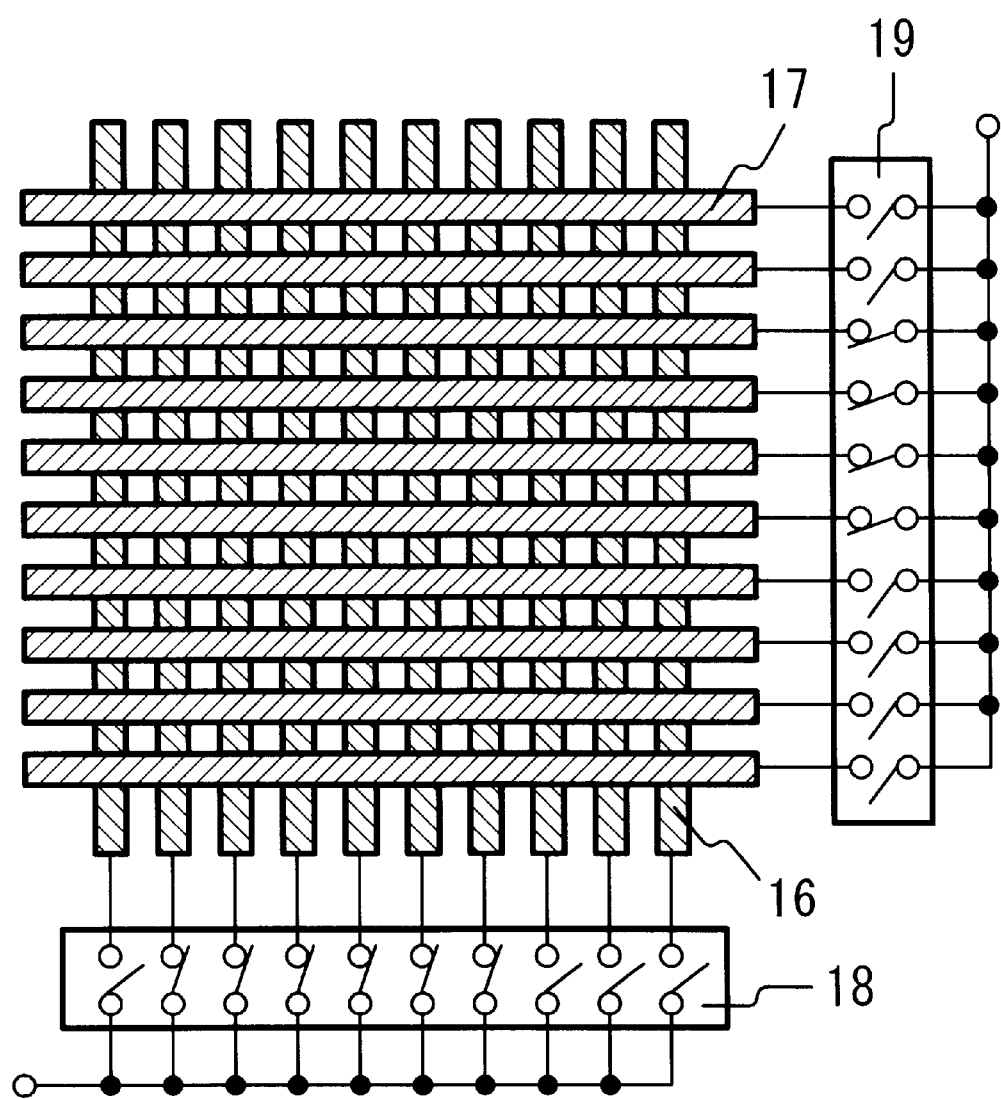
FIG. 23 shows a schematic illustration of first comb-shaped electrode 16 connected with first scanning unit 18, and second comb-shaped electrode 17.

FIG. 23 shows a schematic illustration of first comb-shaped electrode 16 connected with first scanning unit 18, and second comb-shaped electrode 17 connected with second scanning unit 19. First comb-shaped electrode 16 is connected with amplifier 4 via first scanning unit 18, and second comb-shaped electrode 17 is connected with signal analyzer 5 via second scanning unit 19 in FIG. 22. First scanning unit 18 has forty switches corresponding to the electrode-fingers of first comb-shaped electrode 16, respectively. In the same way, second scanning unit 19 has forty switches corresponding to the electrode-fingers of second comb-shaped electrode 17, respectively. The forty switches of first scanning unit 18 form thirty-five groups $X_i$ (i=1, 2, ..., 35), of which each has six switches. In this way, one and the next of the groups $X_i$ have five common switches each other except the first switch of the one of the groups $X_i$ and the last switch of the next of the groups $X_i$. On the other hand, the forty switches of second scanning unit 19 form thirty-seven groups $Y_i$ (i=1, 2, ..., 37) under a condition that each of the groups $Y_i$ has four switches. In this time, one and the next of the groups $Y_i$ have three common switches each other except the first switch of the one of the groups $Y_i$ and the last switch of the next of the groups $Y_i$.

In the ultrasound radiating and receiving device in FIG. 22, if input electric signals are applied between counter electrode 3 and first comb-shaped electrode 16 via the groups $X_i$ in turn, thirty-five longitudinal waves along the direction vertical to the lower end surface of first piezoelectric substrate 12 are radiated into the material in turn. In this way, the thirty-five longitudinal waves are radiated in the form of a scanned ultrasound beam as a whole into the material through silicone rubber 9. When the material is water, the condition of $P/T<4V_w/V$ enables a radiation of the scanned ultrasound beam along the direction vertical to the lower end surface of first piezoelectric substrate 12 into water.

If the scanned ultrasound beam is reflected at an object located inside the material, as shown in FIG. 22, a reflected and scanned ultrasound beam is detected as a scanned electric signal between counter electrode 3 and second comb-shaped electrode 17 by means of each of the groups $Y_i$. In other words, thirty-seven reflected and scanned ultrasound beams are detected as thirty-seven scanned electric signals between counter electrode 3 and second comb-shaped electrode 17 by means of the thirty-seven groups $Y_i$ in turn. As a result, the upper-surface shape of the object is imaged from the scanned electric signals at signal analyzer 5.

On the other hand, the scanned electric signals are amplified via amplifier 4, as well as detected at signal analyzer 5. Thus, amplified electric signals are supplied to first comb-shaped electrode 16 as the input electric signals again. As a result, first comb-shaped electrode 16, amplifier 4, and second comb-shaped electrode 17 form a self-oscillation type of delay-line oscillator.

Figure 24:
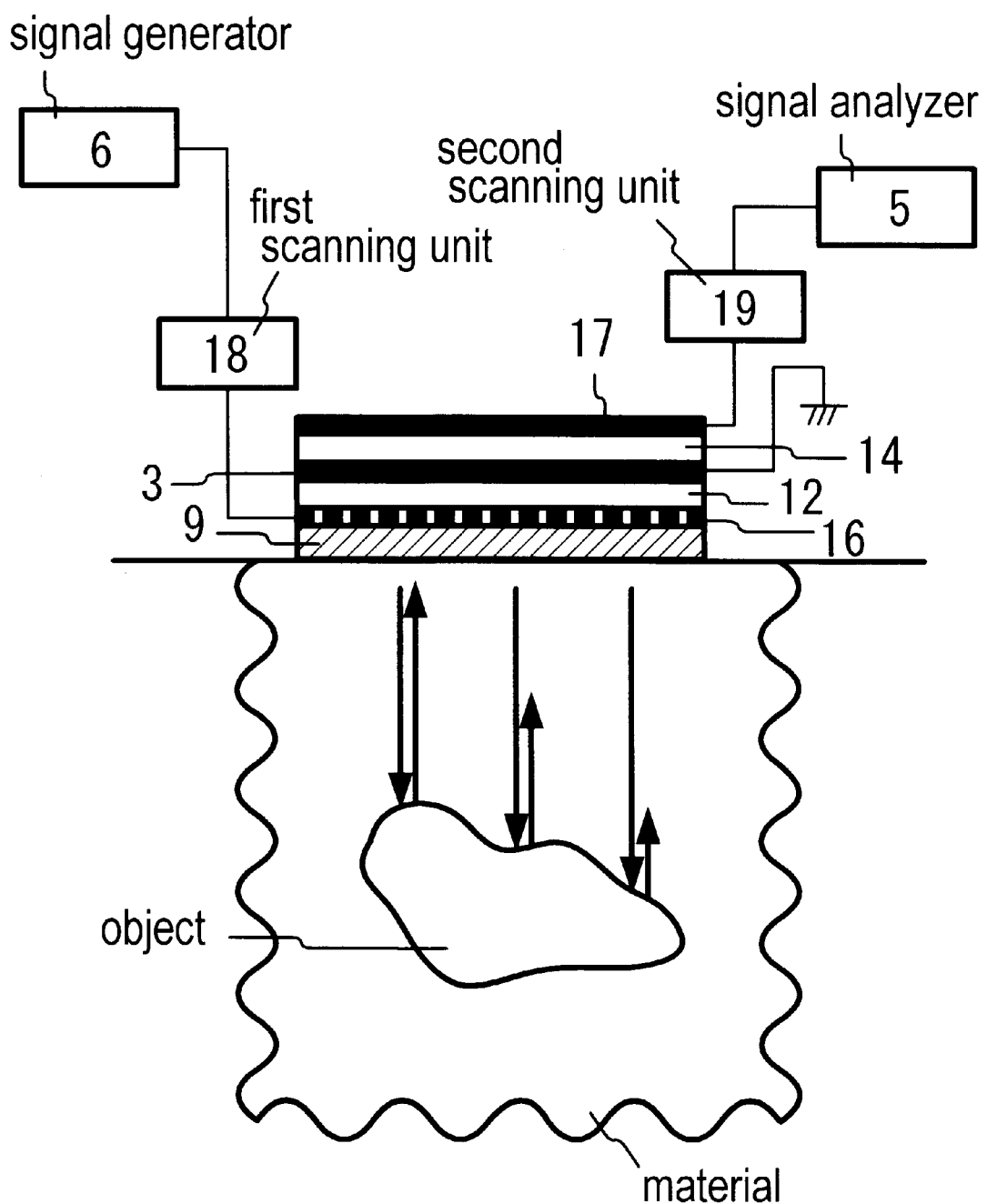
FIG. 24 shows a sectional view of an ultrasound radiating and receiving device according to a fourteenth embodiment of the present invention.

FIG. 24 shows a sectional view of an ultrasound radiating and receiving device according to a fourteenth embodiment of the present invention. The ultrasound radiating and receiving device has the same construction as FIG. 22 except for the absence of amplifier 4 and the presence of signal generator 6.

In the ultrasound radiating and receiving device in FIG. 24, if input electric signals from signal generator 6 are applied between counter electrode 3 and first comb-shaped electrode 16 via the groups $X_i$ in turn, thirty-five longitudinal waves along the direction vertical to the lower end surface of first piezoelectric substrate 12 are radiated into the material in turn. In this way, the thirty-five longitudinal waves are radiated in, the form of a scanned ultrasound beam as a whole into the material through silicone rubber 9. If the scanned ultrasound beam is reflected at an object located inside the material, as shown in FIG. 24, a reflected and scanned ultrasound beam is detected as a scanned electric signal between counter electrode 3 and second comb-shaped electrode 17 by means of each of the groups $Y_i$. In other words, thirty-seven reflected and scanned ultrasound beams are detected as thirty-seven scanned electric signals between counter electrode 3 and second comb-shaped electrode 17 by means of the thirty-seven groups $Y_i$ in turn. And then, the scanned electric signals arrive at signal analyzer 5. As a result, the upper-surface shape of the object is imaged from the scanned electric signals.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. An ultrasound radiating and receiving device comprising:
   a piezoelectric substrate;
   a first comb-shaped electrode formed on an upper end surface of said piezoelectric substrate;
   a second comb-shaped electrode formed on said upper end surface of said piezoelectric substrate; and
   a counter electrode formed on a lower end surface of said piezoelectric substrate and in contact with a surface-part of a material through the lower end surface of said counter electrode,
   said first- and second comb-shaped electrodes forming an interdigital arrangement,
   said first comb-shaped electrode and said counter electrode receiving an input electric signal, radiating a longitudinal wave into said material through said surface-part of said material along the direction vertical to said lower end surface of said piezoelectric substrate, and making an object located inside said material reflect said longitudinal wave back,
   said second comb-shaped electrode and said counter electrode detecting a reflected longitudinal wave as a delayed electric signal.

2. An ultrasound radiating and receiving device as defined in claim 1 further comprising an amplifier between said first- and second comb-shaped electrodes,
   said amplifier amplifying said delayed electric signal, and supplying said first comb-shaped electrode with an amplified electric signal as said input electric signal.

3. An ultrasound radiating and receiving device as defined in claim 1, wherein the opposite surface-part of said material acts as said object.

4. An ultrasound radiating and receiving device as defined in claim 1, wherein the ratio of the interdigital periodicity of said interdigital arrangement to the thickness of said piezoelectric substrate is smaller than four times the ratio of the longitudinal wave velocity in said material to the longitudinal wave velocity in said piezoelectric substrate.

5. An ultrasound radiating and receiving device as defined in claim 1, wherein increasing the number of electrode-finger pairs in said interdigital arrangement makes the directionality of said longitudinal wave sharper under a condition that the total amount of all the finger-areas of said first comb-shaped electrode is constant.

6. An ultrasound radiating and receiving device as defined in claim 1, wherein said material is a liquid matter.

7. An ultrasound radiating and receiving device as defined in claim 1, wherein said material is a cellular tissue.

8. An ultrasound radiating and receiving device as defined in claim 1 further comprising a polymer film, with which said lower end surface of said counter electrode is coated.

9. An ultrasound radiating and receiving device as defined in claim 1 further comprising:
   a scanning unit composed of groups $X_i$ (i=1, 2, ..., n) of switches corresponding to the electrode-fingers of said first comb-shaped electrode, respectively, one and the next of said groups $X_i$ having common switches each other except the first switch of said one of said groups $X_i$ and the last switch of said next of said groups $X_i$,
   said first comb-shaped electrode and said counter electrode receiving input electric signals via said groups $X_i$ in turn, and radiating longitudinal waves along the direction vertical to said lower end surface of said piezoelectric substrate into said material in the form of a scanned ultrasound beam as a whole, and then making said object reflect said longitudinal waves back,
   said second comb-shaped electrode and said counter electrode detecting a reflected ultrasound beam as a scanned electric signal.

10. An ultrasound radiating and receiving device as defined in claim 1 further comprising:
    a first scanning unit composed of groups $X_i$ (i=1, 2, ..., n) of switches corresponding to the electrode-fingers of said first comb-shaped electrode, respectively, one and the next of said groups $X_i$ having common switches each other except the first switch of said one of said groups $X_i$ and the last switch of said next of said groups $X_i$, and
    a second scanning unit composed of groups $Y_i$ (i=1, 2, ..., n) of switches corresponding to the electrode-fingers of said second comb-shaped electrode, respectively, one and the next of said groups $Y_i$ having common switches each other except the first switch of said one of said groups $Y_i$ and the last switch of said next of said groups $Y_j$, said first comb-shaped electrode, together with said counter electrode, receiving input electric signals via said groups $X_i$ in turn, and radiating longitudinal waves along the direction vertical to said lower end surface of said piezoelectric substrate into said material in the form of a scanned ultrasound beam as a whole, and then making said object reflect said longitudinal waves back, said second comb-shaped electrode, together with said counter electrode, detecting reflected longitudinal waves by means of said groups $Y_i$ in turn in the form of a scanned electric signal as a whole.

11. An ultrasound radiating and receiving device comprising.

a first piezoelectric substrate;

a first interdigital arrangement of two comb-shaped electrodes formed on a lower end surface of said first piezoelectric substrate, a lower end surface of said first interdigital arrangement being in contact with a surface-part of a material;

a second piezoelectric substrate;

a second interdigital arrangement of two comb-shaped electrodes formed on an upper end surface of said second piezoelectric substrate; and a counter electrode cemented between said first- and second piezoelectric substrates, one of said two comb-shaped electrodes in said first interdigital arrangement and said counter electrode receiving an input electric signal, radiating a longitudinal wave into said material through said surface-part of said material along the direction vertical to said lower end surface of said first piezoelectric substrate, and making an object located inside said material reflect said longitudinal wave back, one of said two comb-shaped electrodes in said second interdigital arrangement and said counter electrode detecting a reflected longitudinal wave as a delayed electric signal.

12. An ultrasound radiating and receiving device as defined in claim 11, wherein the finger direction of said second interdigital arrangement is orthogonal to that of said first interdigital arrangement.

13. An ultrasound radiating and receiving device as defined in claim 11, wherein the opposite surface-part of said material acts as said object.

14. An ultrasound radiating and receiving device as defined in claim 11, wherein the finger width in said one of said two comb-shaped electrodes in said first interdigital arrangement is wider than that in the other of said two comb-shaped electrodes in said first interdigital arrangement, and the finger width in said one of said two comb-shaped electrodes in said second interdigital arrangement is wider than that in the other of said two comb-shaped electrodes in said second interdigital arrangement.

15. An ultrasound radiating and receiving device as defined in claim 11, wherein the ratio of the interdigital periodicity of said first interdigital arrangement to the thickness of said first piezoelectric substrate is smaller than four times the ratio of the longitudinal wave velocity in said material to the longitudinal wave velocity in said first piezoelectric substrate.

16. An ultrasound radiating and receiving device as defined in claim 11, wherein increasing the number of electrode-finger pairs in said first interdigital arrangement makes the directionality of said longitudinal wave sharper under a condition that the total amount of all the finger-areas of said one of said two comb-shaped electrodes in said first interdigital arrangement is constant.

17. An ultrasound radiating and receiving device as defined in claim 11, wherein said material is a liquid matter.

18. An ultrasound radiating and receiving device as defined in claim 11, wherein said material is a cellular tissue.

19. An ultrasound radiating and receiving device as defined in claim 11 further comprising a polymer film, with which said lower end surface of said first interdigital arrangement is coated.

20. An ultrasound radiating and receiving device as defined in claim 11 further comprising:

a first scanning unit composed of groups $X_1$ (i=11, ..., n) of switches corresponding to the electrode-fingers, respectively, of said one of said two comb-shaped electrodes in said first interdigital arrangement, one and the next of said groups $X_i$ having common switches each other except the first switch of said one of said groups $X_i$ and the last switch of said next of said groups $X_j$, and a second scanning unit composed of groups $Y_i$ (i=11, ..., n) of switches corresponding to the electrode-fingers, respectively, of said one of said two comb-shaped electrodes in said second interdigital arrangement, one and the next of said groups $Y_i$ having common switches each other except the first switch of said one of said groups $Y_i$ and the last switch of said next of said groups $Y_j$, said one of said two comb-shaped electrodes in said first interdigital arrangement, together with said counter electrode, receiving input electric signals via said groups $X_i$ in turn, and radiating longitudinal waves along the direction vertical to said lower end surface of said first piezoelectric substrate into said material through said surface-part of said material in the form of a scanned ultrasound beam as a whole, and then making said object reflect said scanned ultrasound beam back, said one of said two comb-shaped electrodes in said second interdigital arrangement, together with said counter electrode, detecting reflected and scanned ultrasound beams by means of said groups $Y_i$ in turn as scanned electric signals, and imaging the upper surface-shape of said object from said scanned electric signals.

21. An ultrasound radiating and receiving device comprising:

a first piezoelectric substrate;

a first comb-shaped electrode formed on a lower end surface of said first piezoelectric substrate, a lower end surface of said first comb-shaped electrode being in contact with a surface-part of a material, a second piezoelectric substrate;

a second comb-shaped electrode formed on an upper end surface of said second piezoelectric substrate; and a counter electrode cemented between said first- and second piezoelectric substrates, said first comb-shaped electrode and said counter electrode receiving an input electric signal, radiating a longitudinal wave into said material through said surface-part of said material along the direction vertical to said lower end surface of said first piezoelectric substrate, and making an object located inside said material reflect said longitudinal wave back, said second comb-shaped electrode and said counter electrode detecting a reflected longitudinal wave as a delayed electric signal.

22. An ultrasound radiating and receiving device as defined in claim 21, wherein the finger direction of said second comb-shaped electrode is orthogonal to that of said first comb-shaped electrode.

23. An ultrasound radiating and receiving device as defined in claim 21, wherein the opposite surface-part of said material acts as said object.

24. An ultrasound radiating and receiving device as defined in claim 21, wherein the ratio of the interdigital periodicity of said first comb-shaped electrode to the thickness of said first piezoelectric substrate is smaller than four times the ratio of the longitudinal wave velocity in said material to the longitudinal wave velocity in said first piezoelectric substrate.

25. An ultrasound radiating and receiving device as defined in claim 21, wherein increasing the number of electrode-finger pairs in said first comb-shaped electrode makes the directionality of said longitudinal wave sharper under a condition that the total amount of all the finger-areas of said first comb-shaped electrode is constant.

26. An ultrasound radiating and receiving device as defined in claim 21, wherein said material is a liquid matter.

27. An ultrasound radiating and receiving device as defined in claim 21, wherein said material is a cellular tissue.

28. An ultrasound radiating and receiving device as defined in claim 21 further comprising a polymer film, with which said lower end surface of said first comb-shaped electrode is coated.

29. An ultrasound radiating and receiving device as defined in claim 21 further comprising:

a first scanning unit composed of groups $X_i$ (i=1, 2, ... , n) of switches corresponding to the electrode-fingers, respectively, of said first comb-shaped electrode, one and the next of said groups $X_i$ having common switches each other except the first switch of said one of said groups $X_i$ and the last switch of said next of said groups $X_i$, and a second scanning unit composed of groups $Y_i$ (i=1, 2, ... , n) of switches corresponding to the electrode-fingers, respectively, of said second comb-shaped electrode, one and the next of said groups $Y_i$ having common switches each other except the first switch of said one of said groups $Y_i$ and the last switch of said next of said groups $Y_i$, said first comb-shaped electrode and said counter electrode receiving input electric signals via said groups $X_i$ in turn, and radiating longitudinal waves along the direction vertical to said lower end surface of said first piezoelectric substrate into said material through said surface-part of said material in the form of a scanned ultrasound beam as a whole, and then making said object reflect said scanned ultrasound beam back, said second comb-shaped electrode and said counter electrode detecting reflected and scanned ultrasound beams by means of said groups $Y_i$ in turn as scanned electric signals, and imaging the upper surface-shape of said object from said scanned electric signals.

* * * * *